United States Patent
Wayama et al.

(10) Patent No.: US 9,948,871 B2
(45) Date of Patent: Apr. 17, 2018

(54) RADIATION IMAGING APPARATUS AND RADIATION IMAGING SYSTEM

(71) Applicant: CANON KABUSHIKI KAISHA, Tokyo (JP)

(72) Inventors: Hiroshi Wayama, Honjo (JP); Minoru Watanabe, Honjo (JP); Keigo Yokoyama, Honjo (JP); Masato Ofuji, Takasaki (JP); Jun Kawanabe, Kumagaya (JP); Kentaro Fujiyoshi, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/802,297

(22) Filed: Jul. 17, 2015

(65) Prior Publication Data
US 2016/0025865 A1   Jan. 28, 2016

(30) Foreign Application Priority Data

Jul. 25, 2014 (JP) ................................ 2014-152401
Aug. 6, 2014 (JP) ................................ 2014-160799

(51) Int. Cl.
*H04N 5/32* (2006.01)
*A61B 6/00* (2006.01)

(52) U.S. Cl.
CPC .............. *H04N 5/32* (2013.01); *A61B 6/542* (2013.01); *A61B 6/4233* (2013.01); *A61B 6/467* (2013.01); *A61B 6/544* (2013.01); *A61B 6/545* (2013.01)

(58) Field of Classification Search
CPC .. G01T 1/12; G01T 1/026; H04N 5/32; A61B 6/542
See application file for complete search history.

(56) References Cited

U.S. PATENT DOCUMENTS

| | | | |
|---|---|---|---|
| 7,514,663 B2 | 4/2009 | Yagi et al. | 250/208.1 |
| 7,541,591 B2 | 6/2009 | Endo et al. | 250/369 |
| 8,829,438 B2 | 9/2014 | Sato et al. | 250/336.1 |
| 9,101,328 B2 * | 8/2015 | Tsuji | G01T 1/026 |
| 2011/0317054 A1 | 12/2011 | Kameshima et al. | 348/302 |

FOREIGN PATENT DOCUMENTS

JP   2013-176544 A   9/2013

* cited by examiner

*Primary Examiner* — David Porta
*Assistant Examiner* — Faye Boosalis
(74) *Attorney, Agent, or Firm* — Fitzpatrick Cella Harper and Scinto

(57) ABSTRACT

A radiation imaging apparatus includes a radiation detection unit including a plurality of sensors which detect radiation, and a monitoring unit which monitors irradiation of radiation based on signals detected by the plurality of sensors. The monitoring unit determines a plurality of effective sensor candidates from the plurality of sensors, and determines effective sensor(s) from effective sensor candidates excluding certain effective sensor candidates of the plurality of effective sensor candidates, the certain effective sensor candidates being an effective sensor candidate which has detected a signal having a maximum value and an effective sensor candidate which has detected a signal having a minimum value. The monitoring unit monitors irradiation of radiation based on signal(s) detected by the effective sensor(s).

47 Claims, 29 Drawing Sheets

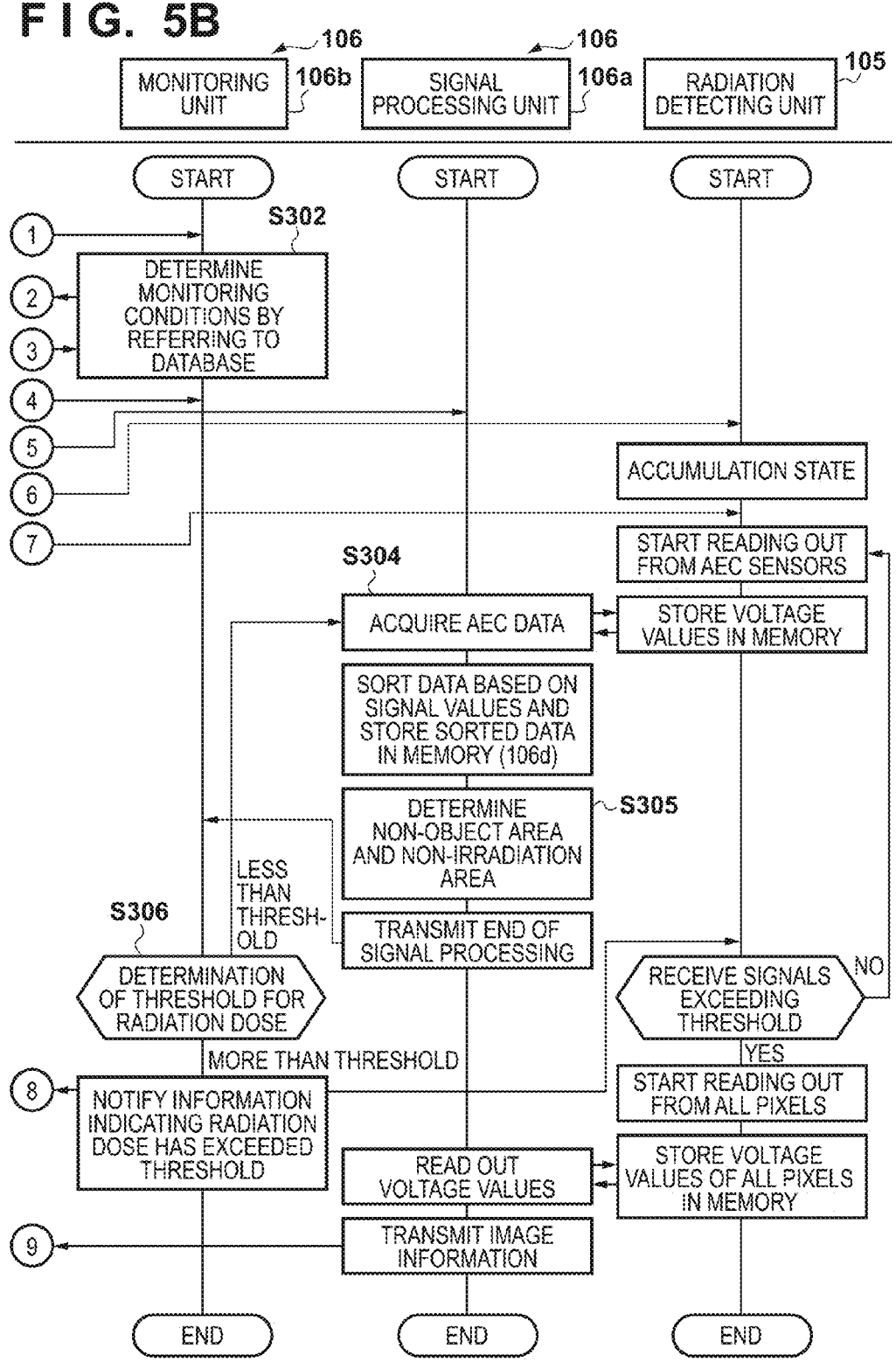

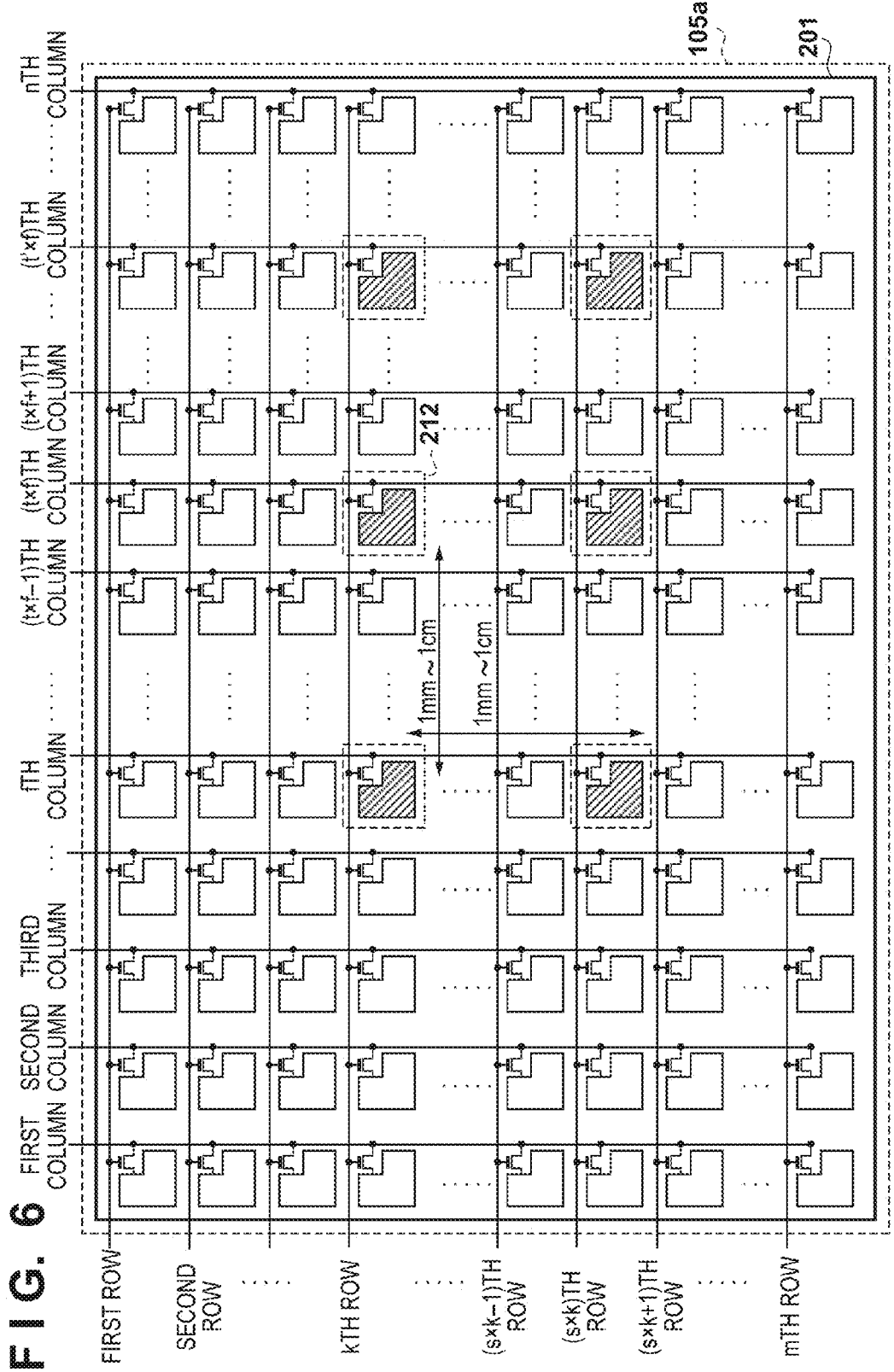

FIG. 7

IMAGING REGION: CHEST PORTION

| SEX | AGE (years) | WEIGHT (kg) | CHEST CIRCUMFERENCE (cm) | ABDOMINAL CIRCUMFERENCE (cm) | AEC SENSORS | MONITORING CONDITIONS (SIGNAL VALUE RANGES) | | |
|---|---|---|---|---|---|---|---|---|
| | | | | | | LUNG FIELD PORTION | RIB PORTION | MEDIASTINUM PORTION |
| ⋮ | ⋮ | ⋮ | ⋮ | ⋮ | ⋮ | ⋮ | ⋮ | ⋮ |
| MALE | 55±10 | 70±10 | 80±10 | 70±10 | STEPS OF 100 PIXELS | 90%-95% | 80%-90% | 5%-15% |
| MALE | 45±10 | 70±10 | 80±10 | 70±10 | STEPS OF 100 PIXELS | 92%-97% | 81%-91% | 4%-14% |
| ⋮ | ⋮ | ⋮ | ⋮ | ⋮ | ⋮ | ⋮ | ⋮ | ⋮ |

HISTOGRAM AT TIME OF CHEST PORTION IMAGING

FIG. 19

| x COORDINATE | y COORDINATE | SIGNAL VALUE | ADDRESS IN MEMORY |
|---|---|---|---|
| 820 | 260 | 9870 | 0x184B70 |
| 450 | 890 | 9054 | 0x184B6A |
| 0 | 40 | 9012 | 0x184B64 |
| 1980 | 2670 | 8756 | 0x184B5E |
| 1260 | 80 | 8045 | 0x184B58 |
| 840 | 920 | 8012 | 0x184B52 |

AVERAGE VALUE

| | | | |
|---|---|---|---|
| 180 | 250 | 345 | 0x170CEC |
| 230 | 980 | 345 | 0x170CE6 |
| 1110 | 680 | 331 | 0x170CE0 |
| 690 | 2500 | 329 | 0x170CDA |
| 2510 | 1570 | 328 | 0x170CD4 |
| 1970 | 660 | 325 | 0x170CCE |

AREA OF EFFECTIVE SENSORS

| | | | |
|---|---|---|---|
| 580 | 780 | 35 | 0x10001E |
| 3000 | 2980 | 21 | 0x100018 |
| 760 | 920 | 15 | 0x100012 |
| 1570 | 780 | 15 | 0x10000C |
| 230 | 1240 | 12 | 0x100006 |
| 250 | 320 | 10 | 0x100000 |

FIG. 23A
FIG. 23B
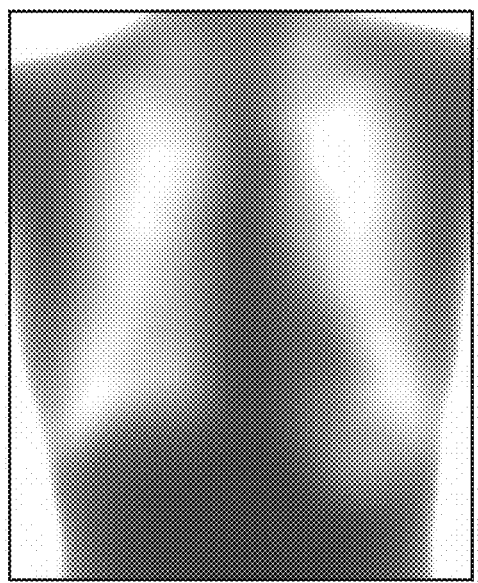
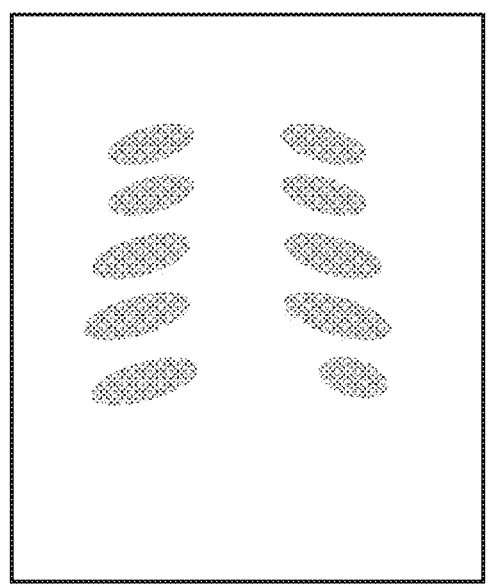

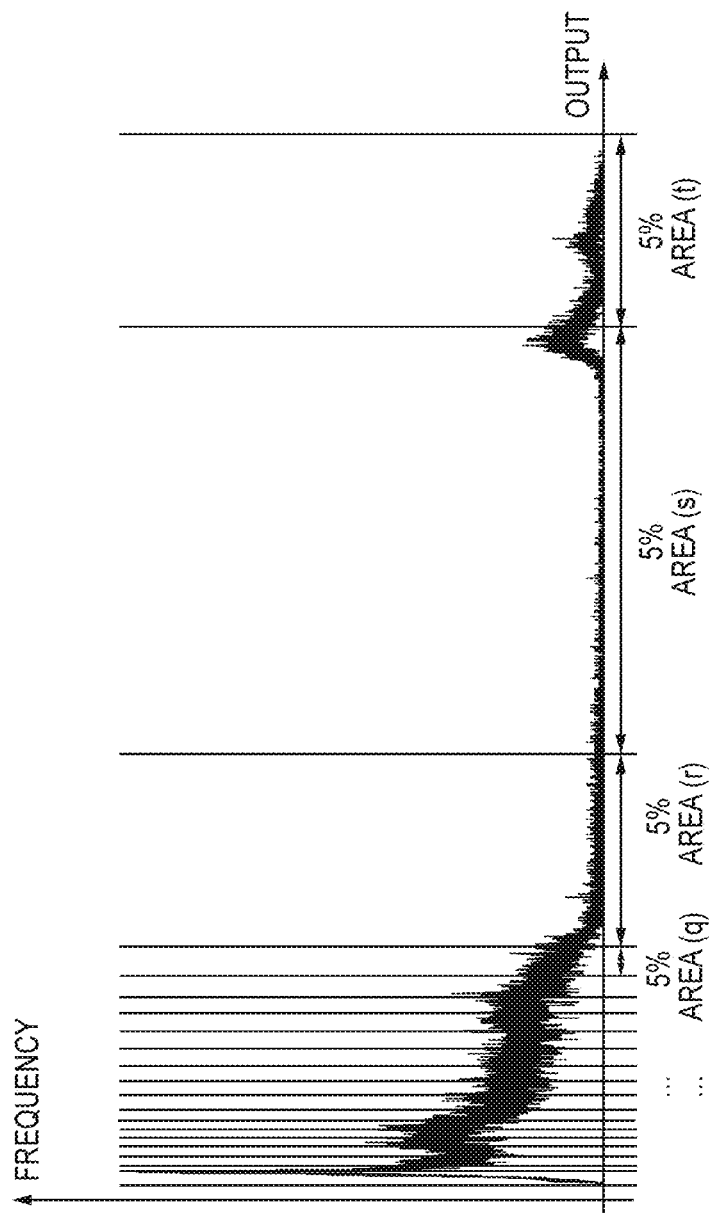

FIG. 25
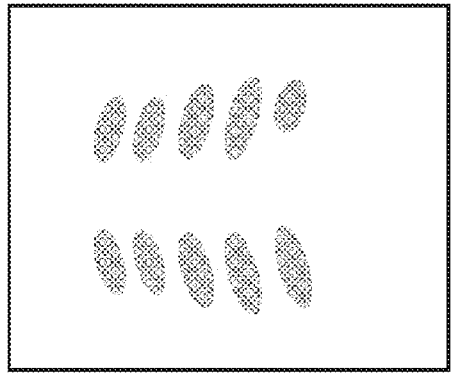
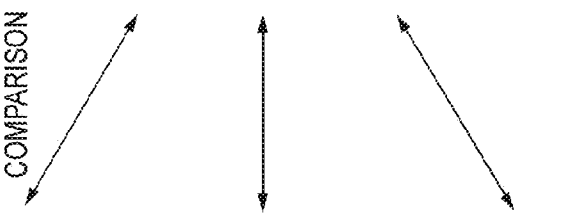

FIG. 26A

MEMORY SPACE IN WHICH REFERENCE IMAGE DATA IS STORED (MEMORY SPACE B)

| x COORDINATE | y COORDINATE | SIGNAL VALUE | ADDRESS IN MEMORY |
|---|---|---|---|
| 3000 | 3000 | 0 | 0x284B70 |
| 3000 | 2990 | 0 | 0x284B6A |
| 3000 | 2980 | 1 | 0x284B64 |
| 3000 | 2970 | 0 | 0x284B5E |
| 3000 | 2960 | 0 | 0x284B58 |
| 3000 | 2950 | 0 | 0x284B52 |
| ..... | ..... | ..... | ..... |
| ..... | ..... | ..... | ..... |
| 0 | 50 | 1 | 0x20001E |
| 0 | 40 | 1 | 0x200018 |
| 0 | 30 | 0 | 0x200012 |
| 0 | 20 | 0 | 0x20000C |
| 0 | 10 | 0 | 0x200006 |
| 0 | 0 | 0 | 0x200000 |

→ (19)

MEMORY SPACE IN WHICH AEC DATA SORTED ACCORDING TO SIGNAL VALUES ARE STORED (MEMORY SPACE A)

20 DIVISIONS

5% AREA (t) OF TOTAL AREA ⇒ VISUALIZATION

5% AREA (k) OF TOTAL AREA ⇒ VISUALIZATION

5% AREA (a) OF TOTAL AREA ⇒ VISUALIZATION

| x COORDINATE | y COORDINATE | SIGNAL VALUE | ADDRESS IN MEMORY |
|---|---|---|---|
| 820 | 260 | 9870 | 0x184B70 |
| 450 | 890 | 9054 | 0x184B6A |
| 0 | 40 | 9012 | 0x184B64 |
| 1980 | 2670 | 8756 | 0x184B5E |
| 1260 | 80 | 8045 | 0x184B58 |
| 840 | 920 | 8012 | 0x184B52 |
| ..... | ..... | ..... | ..... |
| 580 | 780 | 35 | 0x10001E |
| 3000 | 2490 | 21 | 0x100018 |
| 760 | 920 | 15 | 0x100012 |
| 1570 | 780 | 15 | 0x10000C |
| 230 | 1240 | 12 | 0x100006 |
| 250 | 320 | 10 | 0x100000 |

1. SEARCH FOR MATCHING COORDINATES

FIG. 26B

MEMORY SPACE IN WHICH COMPARISON RESULTS ARE STORED
* ARRANGEMENT OF COORDINATES IS IDENTICAL TO THAT IN MEMORY SPACE A (MEMORY SPACE C)

| | x COORDINATE | y COORDINATE | SIGNAL VALUE | ADDRESS IN MEMORY |
|---|---|---|---|---|
| AREA (t) | 820 | 260 | 0 | 0x384B70 |
| | 450 | 890 | 0 | 0x384B6A |
| | 0 | 40 | 1 | 0x384B64 |
| | 1980 | 2670 | 0 | 0x384B5E |
| | 1260 | 80 | 0 | 0x384B58 |
| | 840 | 920 | 1 | 0x384B52 |
| AREA (k) | ..... | ..... | ..... | ..... |
| AREA (a) | 580 | 780 | 0 | 0x30001E |
| | 3000 | 2490 | 1 | 0x300018 |
| | 760 | 920 | 0 | 0x300012 |
| | 1570 | 780 | 0 | 0x30000C |
| | 230 | 1240 | 0 | 0x300006 |
| | 250 | 320 | 0 | 0x300000 |

(19)

2. IF SIGNAL VALUE IN MEMORY SPACE B IS 1, DETERMINATION VALUE IN MEMORY SPACE C IS SET TO 1, WHEREAS IF SIGNAL VALUE IN MEMORY SPACE B IS 0, DETERMINATION VALUE IN MEMORY SPACE C IS SET TO 0

3. AREA WHERE TOTAL OF DETERMINATION VALUES IS LARGEST IS AREA INDICATING AEC TARGET REGION

FIG. 27

MEMORY SPACE IN WHICH AEC DATA REARRANGED IN OUTPUT ORDER ARE STORED
(MEMORY SPACE A)

| x COORDINATE | y COORDINATE | SIGNAL VALUE | ADDRESS IN MEMORY | |
|---|---|---|---|---|
| 820 | 260 | 9870 | 0x184B70 | 20 DIVISIONS |
| 450 | 890 | 9054 | 0x184B6A | |
| 0 | 40 | 9012 | 0x184B64 | 5% AREA (t) OF TOTAL AREA |
| 1980 | 2670 | 8756 | 0x184B5E | |
| 1260 | 80 | 8045 | 0x184B58 | |
| 840 | 920 | 8012 | 0x184B52 | |

AVERAGE VALUE

| | | | | |
|---|---|---|---|---|
| 180 | 250 | 345 | 0x170CEC | |
| 230 | 980 | 345 | 0x170CE6 | |
| 1110 | 680 | 331 | 0x170CE0 | 5% AREA (k) OF TOTAL AREA |
| 690 | 2500 | 329 | 0x170CDA | |
| 2510 | 1570 | 328 | 0x170CD4 | |
| 1970 | 660 | 325 | 0x170CCE | |

AEC TARGET AREA

| | | | | |
|---|---|---|---|---|
| 580 | 780 | 35 | 0x10001E | |
| 3000 | 2980 | 21 | 0x100018 | |
| 760 | 920 | 15 | 0x100012 | 5% AREA (a) OF TOTAL AREA |
| 1570 | 780 | 15 | 0x10000C | |
| 230 | 1240 | 12 | 0x100006 | |
| 250 | 320 | 10 | 0x100000 | |

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

Recently, radiation imaging apparatuses have been devised to minimize the exposure dose by properly managing radiation. For example, there is available a method (AEC (Auto Exposure Control)) of automatically stopping the emission of radiation when, for example, the optimal amount of radiation for diagnosis is applied. It is possible to perform proper diagnosis with the minimum necessary radiation dose by stopping the emission of radiation when a specific region of a patient which is designated by a doctor or radiation technician is irradiated with a predetermined amount of radiation. When performing AEC, it is necessary to properly determine with which region of a patient has been irradiated how much amount of radiation.

Japanese Patent Laid-Open No. 2013-176544 discloses a radiation imaging apparatus which performs auto exposure control. This radiation imaging apparatus divides an irradiation field into a non-object area, an implant area, and an object area based on a histogram. This apparatus then specifies the minimum value pixel and the maximum value pixel in the object area, and stops the emission of radiation based on the integrated pixel values of the minimum value pixel and the maximum value pixel. In this case, a non-object area is defined as an area directly irradiated with radiation without transmission through an object, an implant area is defined as an area where an implant exists in the object, and an object area is defined as an area obtained by excluding the non-object area and the implant area from the irradiation field.

The apparatus disclosed in Japanese Patent Laid-Open No. 2013-176544 divides an irradiation field into a non-object area, an implant area, and an object area based on a histogram. In practice, however, there is an area which should not be classified to either a non-object area or an object area. When taking chest portion imaging as an example, an area having a pixel value which is the second largest to a non-object area is not a lung field area but is the boundary area between the non-object area and the skin of the object. Therefore, on a histogram with one axis representing pixel values and the other axis presenting frequencies in pixel value classes, the boundary area is located between the non-object area and the object area.

The apparatus disclosed in Japanese Patent Laid-Open No. 2013-176544 detects the maximum peak, of the peaks of a histogram, which indicates the maximum pixel value, uses, as a non-object threshold, a pixel value obtained by multiplying the pixel value of the maximum peak by the ratio of pixels located in the negative direction relative to the pixel value, and specifies, as a non-object area, an area exhibiting pixel values equal to or more than the non-object threshold in the irradiation field. In addition, the scheme disclosed in Japanese Patent Laid-Open No. 2013-176544 is designed to stop the emission of radiation based on the integrated pixel value of a maximum value pixel in an object area adjacent to a non-object area on a histogram. However, the maximum value pixel is likely to be a pixel in a boundary area. In such a method, therefore, the accuracy of exposure control is low. The same applies to the determination of a minimum value pixel.

In addition, even if no non-object area exists, exposure control should not be performed by using pixels in a specific range including the maximum value pixel. If no non-object area exists, it can be considered that a maximum value pixel is located at a specific region in an irradiation area. The radiation emitted from a radiation source has a spatial distribution, and radiation having a very high output is sometime generated in a partial area. In this case, there is a possibility that a maximum value pixel is a pixel located at a position different from the position of a region targeted by a doctor or radiation technician.

Furthermore, likewise, in a case in which there is no non-irradiation area such as an implant area, exposure control should not be performed by using pixels in a specific range including the minimum value pixel. Since the pixel value of the minimum value pixel includes a large noise component, the accuracy of exposure control based on the pixel value of the minimum value pixel is low.

SUMMARY OF THE INVENTION

One embodiment of the present invention provides a technique advantageous in improving the accuracy of exposure control.

One embodiments of the present invention provides a radiation imaging apparatus comprising: a radiation detection unit including a plurality of sensors which detect radiation; and a monitoring unit which monitors irradiation of radiation based on signals detected by the plurality of sensors, wherein the monitoring unit determines a plurality of effective sensor candidates from the plurality of sensors, and determines effective sensor(s) from effective sensor candidates excluding certain effective sensor candidates of the plurality of effective sensor candidates, the certain effective sensor candidates being an effective sensor candidate which has detected a signal having a maximum value and an effective sensor candidate which has detected a signal having a minimum value, and wherein the monitoring unit monitors irradiation of radiation based on signal(s) detected by the effective sensor(s).

Further features of the present invention will become apparent from the following description of exemplary embodiments with reference to the attached drawings.

BRIEF DESCRIPTION OF THE DRAWINGS

FIGS. 5A and 5B are block diagrams showing the operation of the radiation imaging system according to the embodiment of the present invention;

FIG. 6 is a view exemplarily showing pixels (sensors) used for an AEC operation;

FIG. 7 is a view exemplarily showing a database;

FIG. 19 is a view exemplarily showing the selection of effective sensors used for AEC;

FIGS. 23A and 23B are views exemplarily showing a radiation image and a reference image of the chest portion;

FIG. 24 is a view exemplarily showing a histogram of AEC data (the signals detected by sensors 212);

FIG. 25 is a view schematically showing a method of determining monitoring sensors;

FIGS. 26A and 26B are views schematically showing a method of determining monitoring sensors; and FIG. 27 is a view schematically showing a method of determining monitoring sensors.

DESCRIPTION OF THE EMBODIMENTS

The present invention will be described below through its exemplary embodiments with reference to the accompanying drawings.

Figure 2:
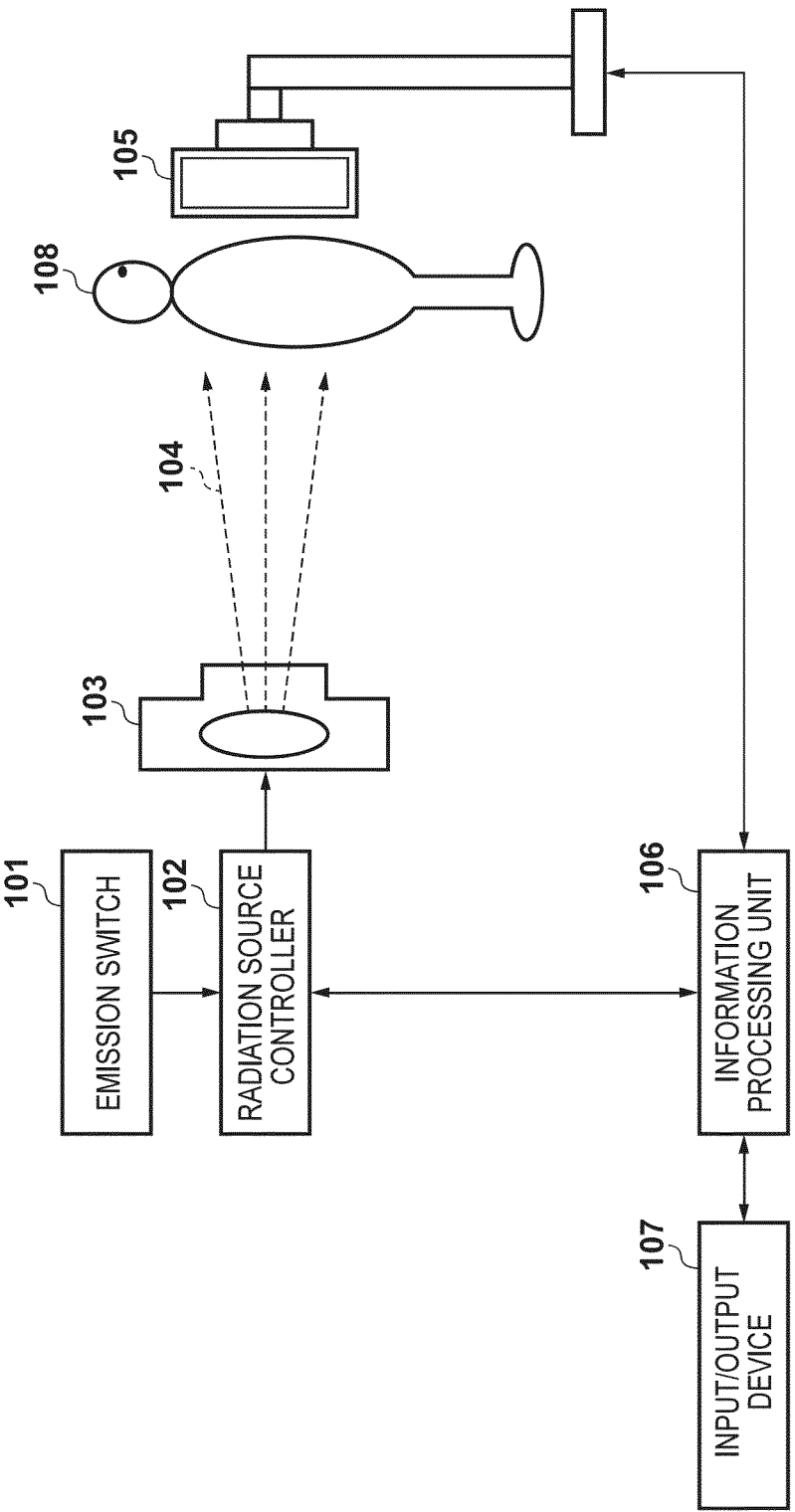
FIG. 2 is a block diagram showing the arrangement of a radiation imaging system according to the embodiment of the present invention.

The arrangement of a radiation imaging system 100 according to the first embodiment of the present invention will be described with reference to FIG. 2. The radiation imaging system 100 includes an emission switch 101, a radiation source controller 102, a radiation source 103, a radiation detection unit 105, an information processing unit 106, and an input/output device 107. The emission switch 101 is a switch which is connected to the radiation source controller 102 via a wired cable or wirelessly and used to issue an instruction to obtain a radiation image (to emit radiation 104 from the radiation source 103 and obtain a radiation image by using the radiation detection unit 105).

The radiation source controller 102 is connected to the emission switch 101, the radiation source 103, and the information processing unit 106, and controls the radiation source 103. The radiation source controller 102 causes the radiation source 103 to emit the radiation 104 (irradiate a patient 108) in response to the signal transmitted from the emission switch 101. The information processing unit 106 is connected to the input/output device 107 and the radiation detection unit 105 and causes the radiation source controller 102 to stop the emission of radiation (irradiation on the patient 108) in response to a signal from the radiation detection unit 105. That is, the information processing unit 106 performs an AEC operation. In addition, the information processing unit 106 stores the radiation image generated based on a signal from the radiation detection unit 105 in a memory or causes the input/output device 107 to display the image.

Figure 3:
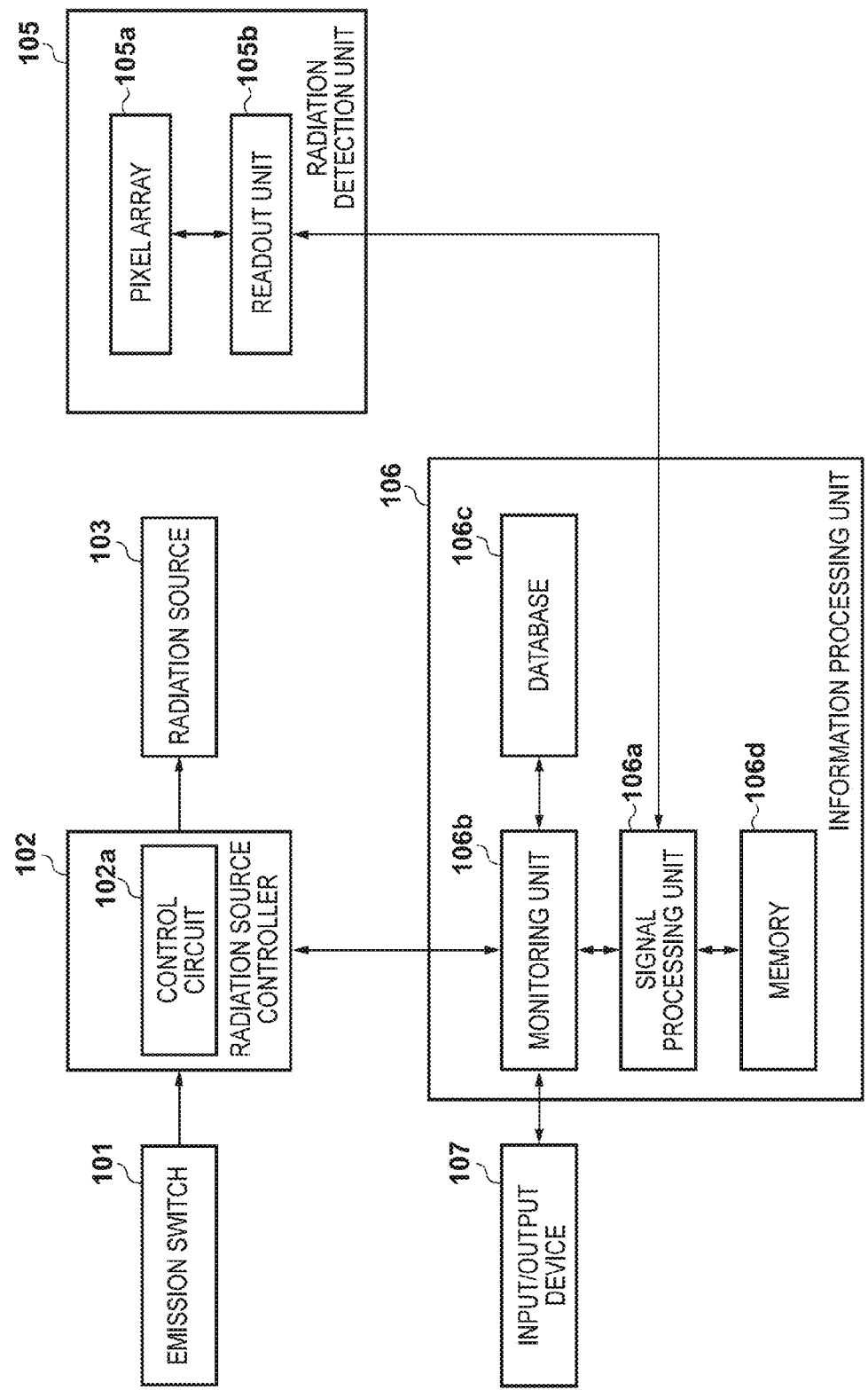
FIG. 3 is a block diagram showing the concrete arrangement of the radiation imaging system according to the embodiment of the present invention.

The description will be continued with reference to FIG. 3. The radiation source controller 102 includes a control circuit 102a which controls the radiation source 103. The information processing unit 106 includes a signal processing unit 106a, a monitoring unit 106b, and a database 106c, and performs an AEC operation. The monitoring unit 106b is connected to the signal processing unit 106a and the database 106c. The signal processing unit 106a is connected to a memory 106d. The radiation detection unit 105 includes a pixel array 105a and a readout unit 105b. The pixel array 105a is a device including a plurality of pixels for obtaining radiation images. The pixel array 105a is also a device including a plurality of sensors which detect radiation. The plurality of sensors may be used as pixels for obtaining radiation images or may be dedicated sensors for detecting radiation. The readout unit 105b reads out signals from the pixel array 105a and outputs them to the information processing unit 106. The signal processing unit 106a can include a function of sorting, for example, the signals output from the radiation detection unit 105 based on their values.

The information processing unit 106 can be formed by installing programs (software) in a general-purpose computer. Alternatively, the information processing unit 106 can be formed as a device including the monitoring unit 106b formed by installing programs in a general-purpose computer and the signal processing unit 106a formed by installing programs in a general-purpose computer. Such programs or a memory medium storing the programs can also constitute the present invention. Alternatively, the information processing unit 106 can be implemented by a circuit designed or programmed to implement the function (for example, an ASIC (Application Specific Integrated Circuit) or PLD (Programmable Logic Device). Alternatively, the monitoring unit 106b and the signal processing unit 106a constituting the information processing unit 106 each can be implemented by a circuit designed to implement the corresponding function (for example, an ASIC or PLD).

Figure 4:
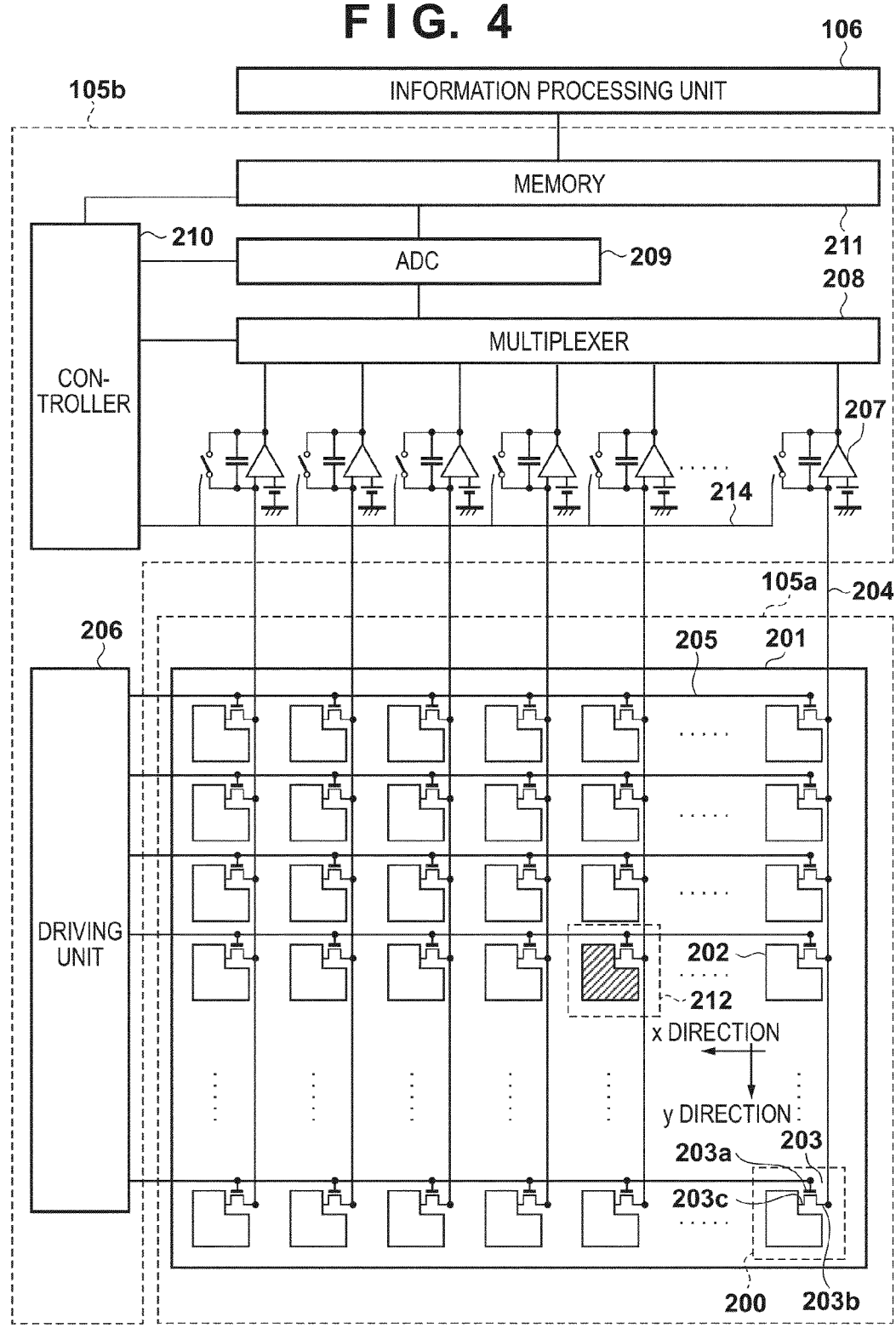
FIG. 4 is a view showing the arrangement of a radiation detection unit according to the embodiment of the present invention.

The arrangement of the radiation detection unit 105 will be described with reference to FIG. 4. The radiation detection unit 105 includes the pixel array 105a and the readout unit 105b. The pixel array 105a may be of a direct type which directly converts radiation into electrical signals or an indirect type which converts radiation into visible light and then converts the visible light into electrical signals. When using an indirect type, radiation is converted into visible light by a scintillator (not shown). Typically, the scintillator can be arranged on the entire area of the pixel array 105a. The scintillator can be formed from, for example, GOS (gadolinium oxysulfide) or CsI (cesium iodide).

The pixel array 105a can be formed from, for example, an active matrix array 201. The active matrix array 201 includes a plurality of pixels 200 arrayed to form a plurality of rows and a plurality of columns. Each pixel 200 includes a conversion element 202 which outputs an electrical signal (for example, a charge, voltage, or current) in accordance with the amount of incident radiation and a switch 203 which connects the conversion element 202 to a column signal line 204. In the case shown in FIG. 4, some of the plurality of pixels 200 for obtaining radiation images are used as sensors for AEC, that is, for detecting radiation. Pixels of the plurality of pixels 200, which are used as sensors can be arbitrarily determined.

The position of each pixel 200 can be specified by the position (column number) in the x direction (row direction) and the position (row number) in the y direction (column direction), that is, the coordinates. For example, the number of pixels in the x direction and the number of pixels in the y direction are 1,000 to 4,000, and hence the total number of pixels is about 10,000,000. The switch 203 is a transistor having a gate 203a, a source 203b, and a drain 203c. A driving unit 206 controls each switch 203 via a driving line 205 connected to the gate 203a. The drain 203c of each switch 203 is connected to the conversion element 202, and the source 203b of the switch is connected to the column signal line 204.

Each conversion element 202 can be a PIN conversion element (PIN photodiode) formed by stacking a p-type semiconductor, an intrinsic semiconductor, and an n-type semiconductor or a MIS conversion element formed by stacking an n-type semiconductor, an intrinsic semiconductor, and an insulator. The conversion element 202 has electrodes on its upper and lower portions. The potential of one electrode is fixed via a bias line (not shown), the other electrode is floated while being given a predetermined potential. This generates an electric field in the conversion element 202. In this state, pairs of electrons and holes are generated by the incidence of light when using a direct type, and are generated by the incidence of visible light when using an indirect type. These electrons and holes move in opposite directions along an electric field. Of electrons and holes, charges which have moved to the floated electrode are accumulated. When the conversion element 202 is of a direct type, amorphous selenium is preferably used as a semiconductor material for the conversion element 202. When the conversion element 202 is of an indirect type, amorphous silicon or polysilicon is preferably used as a semiconductor material for the conversion element 202. Each switch 203 is formed from a transistor such as a thin-film transistor. The thin film transistor may be, for example, a bottom gate type thin-film transistor having the driving line 205 located below the thin-film transistor, or may be a top gate type thin-film transistor having the driving line 205 located above the thin-film transistor. The conversion element 202 and the switch 203 can be generally formed by using a CVD (Chemical Vapor Deposition) apparatus.

The readout unit 105b includes the driving unit 206, an amplification unit 207, a multiplexer 208, an ADC (AD converter) 209, a controller 210, and a memory 211. The driving unit 206 drives the switches 203 via the driving lines 205 provided on the respective rows. The pixels 200 having the switches 203 connected to one driving line 205 constitute one row. When the driving line 205 is driven to an active level, the switches 203 connected to the driving line 205 are turned on to transfer charges in the conversion elements 202 connected to the switches 203 to the amplification units 207 via the column signal lines 204.

The controller 210 controls the amplification unit 207, the multiplexer 208, the ADC 209, and the memory 211. Each amplification unit 207 converts the charges output from the conversion element 202 into a voltage. The amplification unit 207 is reset when the controller 210 drives a reset line 214 to an active level. The multiplexer 208 sequentially selects the signals in voltage forms output from the plurality of amplification units 207 respectively corresponding to a plurality of columns based on commands from the controller 210, and provides the signals to the ADC 209. The ADC 209 converts each signal in a voltage form into a digital signal and provides it to the memory 211 and the information processing unit 106. The memory 211 holds the signals provided from the ADC 209, that is, the signals read out from the pixels 200, in correspondence with the positions (coordinates) of the pixels 200.

Figure 1:
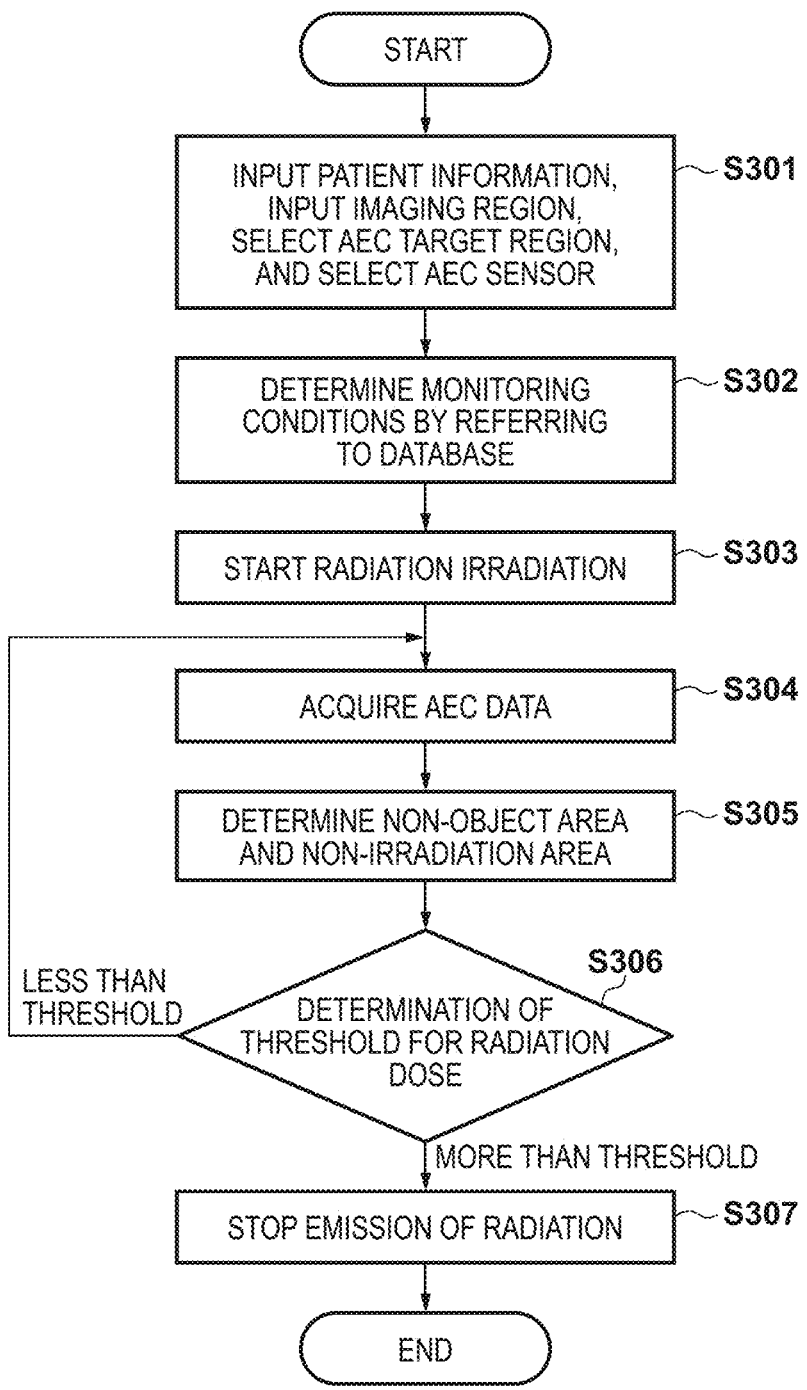
FIG. 1 is a flowchart showing an AEC operation according to an embodiment of the present invention.
Figure 5A:
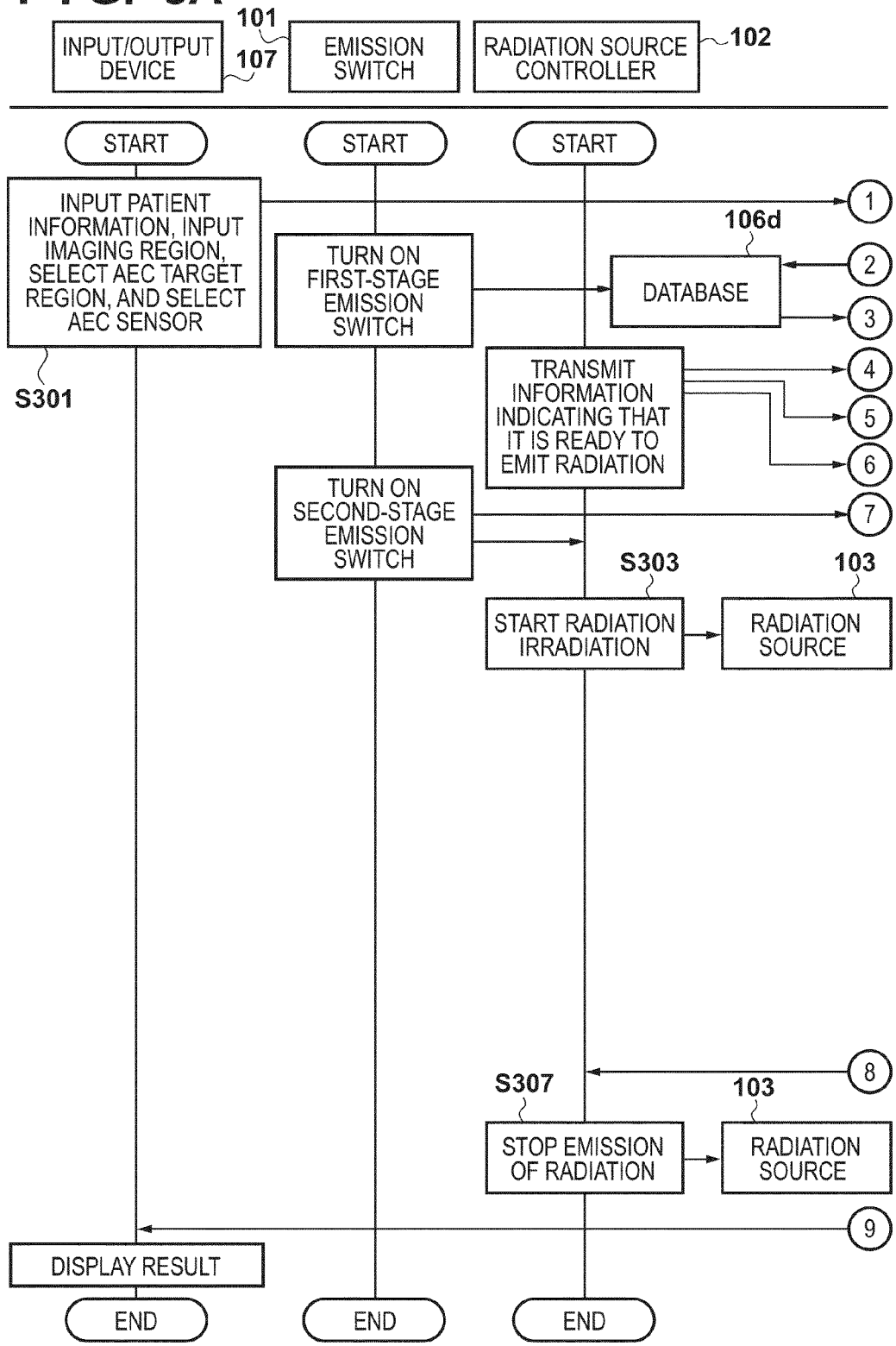

The operation of the radiation imaging system 100 will be described below with reference to FIGS. 1 and 5. Note that FIGS. 5A and 5B show the operations of the input/output device 107, the emission switch 101, the radiation source controller 102, the information processing unit 106, and the radiation detection unit 105 in correspondence with each step in the flowchart of FIG. 1.

In step S301, the doctor or radiation technician provides patient information (object information) to the information processing unit 106 via the input/output device 107. Patient information is, for example, information characterizing an object such as sex, age, weight, chest circumference, and abdominal circumference. More specifically, patient information can be, for example, sex: male, weight: 70 kg, chest circumference: 100 cm, and abdominal circumference: 80 cm. In step S301, the doctor or radiation technician provides imaging region information indicating an imaging region via the input/output device 107. An imaging region is, for example, a head portion, chest portion, or abdominal portion.

In step S301, the input/output device 107 provides information designating an AEC target region used for AEC and the pixels 200 as sensors 212 for AEC to the information processing unit 106. If, for example, an imaging region is a chest portion, an AEC target region is set as a lung field portion, the pixels 200 arranged at intervals of 1 mm to 1 cm in the x direction and the y direction are selected as sensors 212, as exemplarily shown in FIG. 6. Note that if the pixel size is about 150 μm×150 μm, pixels arranged at intervals 1 mm to 1 cm correspond to pixels arranged at intervals of 8 pixels to 80 pixels. In this case, μm indicates micrometer. An AEC target region and the sensors 212 may be selected by the input/output device 107 in accordance with an imaging region or may be selected by the doctor or radiation technician. For example, the input/output device 107 can set an AEC target region and the sensors 212 as defaults. The doctor or radiation technician can change the default AEC target region and the default sensors 212, as needed. Information designating an AEC target region and the sensors 212 is an example of AEC information.

In the case shown in FIG. 6, the sensors 212 are set for every multiple of k, like the kth row, the (2×k)th row, . . . , the interval between the adjacent sensors 212 is set to about 1 mm to 1 cm. However, this is merely an example. It is possible to arbitrarily select sensors 212 from the plurality of pixels 200 constituting the pixel array 105a in accordance with an AEC target region. If, for example, an AEC target region is a lung field portion, the pixels 200 arranged at intervals equal to or less than the size of the lung field portion are preferably determined as the sensors 212. This makes at least one sensor 212 be located within the area of the AEC target region.

In step S302, the monitoring unit 106b determines conditions, of the plurality of conditions registered in the database 106c, which correspond to the information (the patient information, imaging region information, and AEC information) provided in step S301 as monitoring conditions for AEC. FIG. 7 exemplifies information registered in the database 106c. More specifically, FIG. 7 shows the relationship between patient information (sex, age, chest circumference, and abdominal circumference), AEC information (information designating sensors for AEC), and monitoring conditions (the range of signal values) when performing chest circumference imaging (specified by imaging region information).

Monitoring conditions are used to specify effective sensors for AEC from the sensors (to be referred to as effective sensor candidates hereinafter) remained after excluding the sensors 212 located in a non-object area and the sensors 212 located in a non-irradiation area from the sensors 212 designed by AEC information. Assume that an imaging region is a chest portion, and an AEC target region is a lung field portion of a patient with sex: male, weight: 55±10 (kg), chest circumference: 80±10 (cm), abdominal circumference: 70±10 (cm), and AEC sensors: in steps of 100 pixels (for every 100 pixels). In this case, monitoring conditions designate, as effective sensors, effective sensor candidates which have detected signals having values within the range from 90% to 95%, with the minimum and maximum values of the signals detected by a plurality of effective sensor candidates being respectively defined as 0% and 100%. A non-object area is an area, of an imaging area formed by the pixel array 105a, which radiation enters without being transmitted through an object. A non-irradiation area is an area, of the imaging area formed by the pixel array 105a, which is not irradiated with radiation.

All the monitoring conditions are stipulated to determine, as effective sensors, effective sensor candidates, of the plurality of effective sensor candidates which have been designated by AEC information, which exclude an effective sensor candidate which has detected a signal having the minimum value and an effective sensor candidate which has detected a signal having the maximum value. That is, monitoring conditions are stipulated to determine, as effective sensors, effective sensor candidates which have detected signals having values within an arbitrary range from larger than 0% to smaller than 100%, with the minimum and maximum values of the signals detected by a plurality of effective sensor candidates being respectively defined as 0% and 100%. Monitoring conditions are those matching information (patient information, imaging region information, and AEC information), of the plurality of monitoring conditions registered in the database 106c, which are set for obtaining a radiation image. The monitoring unit 106b can determine monitoring conditions by referring to the database 106c.

In step S303, the radiation source 103 is ready to emit the radiation 104. The doctor or radiation technician operates the emission switch 101 to emit radiation from the radiation source 103 and irradiate the patient 108 with the radiation. In general, the emission switch 101 is a two-stage switch. When the first-stage switch is turned on, the radiation source 103 starts a preliminary operation. This preliminary operation is an operation necessary for stable emission of the radiation 104. When the second-stage switch is turned on, the radiation 104 is emitted from the radiation source 103. As shown in FIGS. 5A and 5B, when the first-stage switch of the emission switch 101 is turned on, information indicating that the radiation source 103 has started a preliminary operation is transmitted to the monitoring unit 106b, the signal processing unit 106a, and the radiation detection unit 105.

The readout unit 105b of the radiation detection unit 105 causes the pixels 200 including the sensors 212 to start accumulating charges in response to turn-on of the first-stage switch of the emission switch 101. Thereafter, when the second-stage switch of the emission switch 101 is turned on to emit the radiation 104 from the radiation source 103, the readout unit 105b of the radiation detection unit 105 starts a readout operation for the signals detected by the sensors 212.

Figure 8:
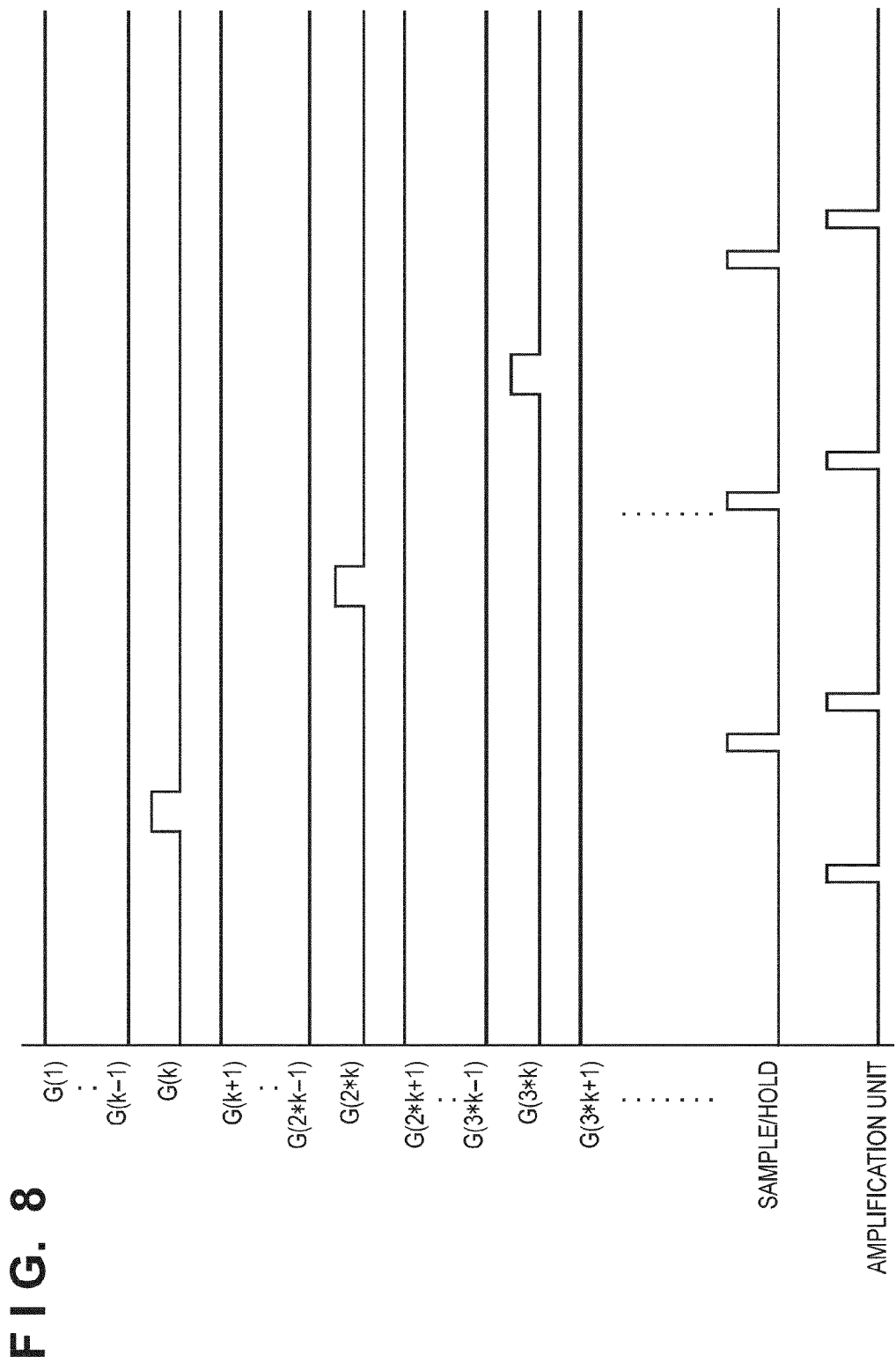
FIG. 8 is a timing chart exemplarily showing the operation of a readout unit.

In step S304, the signal processing unit 106a of the information processing unit 106 acquires the signals detected by the sensors 212, that is, AEC data. FIG. 8 shows a readout operation for signals (detected by the sensors 212) corresponding to the charges accumulated in the sensors 212 of the pixel array 105a. The readout operation is performed with respect to only the AEC sensors 212 of the pixels 200 constituting the pixel array 105a. More specifically, the driving lines 205 on rows defined by multiples of k, like the kth row, the (2×k)th row, the (3×k)th row, . . . , are sequentially driven to an active level in accordance with the coordinates of the sensors 212 shown in FIG. 6. The potential of the remaining driving lines 205 are maintained at an inactive level.

First, the signals detected by the sensors 212 on the kth row are read out. The amplification units 207 are reset. Thereafter, the driving unit 206 drives the driving line 205 on the kth row to an active level to turn on the switches 203 of the sensors 212 on the kth row. When the switches 203 are turned on, the charges accumulated in the conversion elements 202 are transferred to the amplification units 207. A sample/hold circuit (not shown) samples/holds the signals obtained by causing the amplification units 207 to convert charges into analog voltage values D1, D2, D3, . . . . The multiplexer 208 sequentially transmits the signals detected by the sensors 212 on the kth row to the ADC 209, which then converts the analog voltage values D1, D2, D3, . . . into digital voltage values D'1, D'2, and D'3, . . . . The multiplexer 208 is only required to output only signals from the sensors 212, and hence select only the columns on which the sensors 212 exist. Referring to FIG. 6, since the sensors 212 exist for every f columns, the multiplexer 208 sequentially selects the fth column, the (2×f)th column, the (3×f)th column, . . . .

The signals (AEC data) read out in this manner are sequentially stored in the memory 211. In this case, the memory 211 stores the signals (the signals detected by the sensors 212) read out from the sensors 212 in correspondence with the position (coordinate) information of the sensors 212. More specifically, with regard to one sensor 212, a memory space having a total of about six bytes is used: about two bytes for each of positional information in the x direction and positional information in the y direction and about two bytes for the signal read out from the sensor 212 (note that if the resolution of the ADC is 16 bits or more, three bytes or more are used). After a readout operation for the kth row is complete, readout operations are sequentially performed on the (2×k)th row, the (3×k)th row, . . . , and the readout information is stored in the memory 211, together with the positional information of the sensor 212.

In step S305, the signal processing unit 106a determines AEC data, of the AEC data stored in the memory 211, which are detected by the sensors 212 arranged in a non-object area and the sensors 212 arranged in a non-irradiation area. This determination is performed by, for example, generating AEC data stored in the memory 211 and processing the histogram. For example, the information processing unit 106 copies the AEC data stored in the memory 211 and the positional information of the sensors 212 to the memory 106d. Subsequently, as exemplarily shown in FIG. 9, the information processing unit 106 stores the information copied to the memory 106d in another area in the memory 106d, together with positional information, upon sorting the AEC data in ascending order of the values of signals.

In this case, if the AEC data (the signal value detected by the sensor 212) is 5000, the position of the sensor 212 in the x direction is 150, the position of the sensor 212 in the y direction is 300, and the start memory address of the storage destination is 0001, the corresponding information is written as (5000, 150, 300, 0x0001). "Ox" indicates that a memory address is expressed in hexadecimal.

Assume that the following six pieces of information are stored in the memory 106d:
 (5000, 150, 300, 0x0000)
 (6000, 1500, 300, 0x0006)
 (5500, 2850, 300, 0x000C)
 (5800, 150, 2700, 0x0012)
 (6060, 1500, 2700, 0x0018)
 (4800, 2850, 2700, 0x001E)

In this case, the value of each signal can be expressed by two bytes, coordinates are expressed by two bytes, and a memory space of a total of six bytes is used. Since six bytes are used for one sensor 212, the number of memory addresses increases by six per one sensor 212. When these six pieces of information are arranged in ascending order of signal values, these pieces of information are stored in another memory space in the following order:
 (4800, 2850, 2700, 0x1000)
 (5000, 150, 300, 0x1006)
 (5500, 2850, 300, 0x100C)
 (5800, 150, 2700, 0x1012)
 (6000, 1500, 300, 0x1018)
 (6060, 1500, 2700, 0x101E)
This operation is performed for the signals obtained from all the sensors 212 and positional information.

Figure 10:
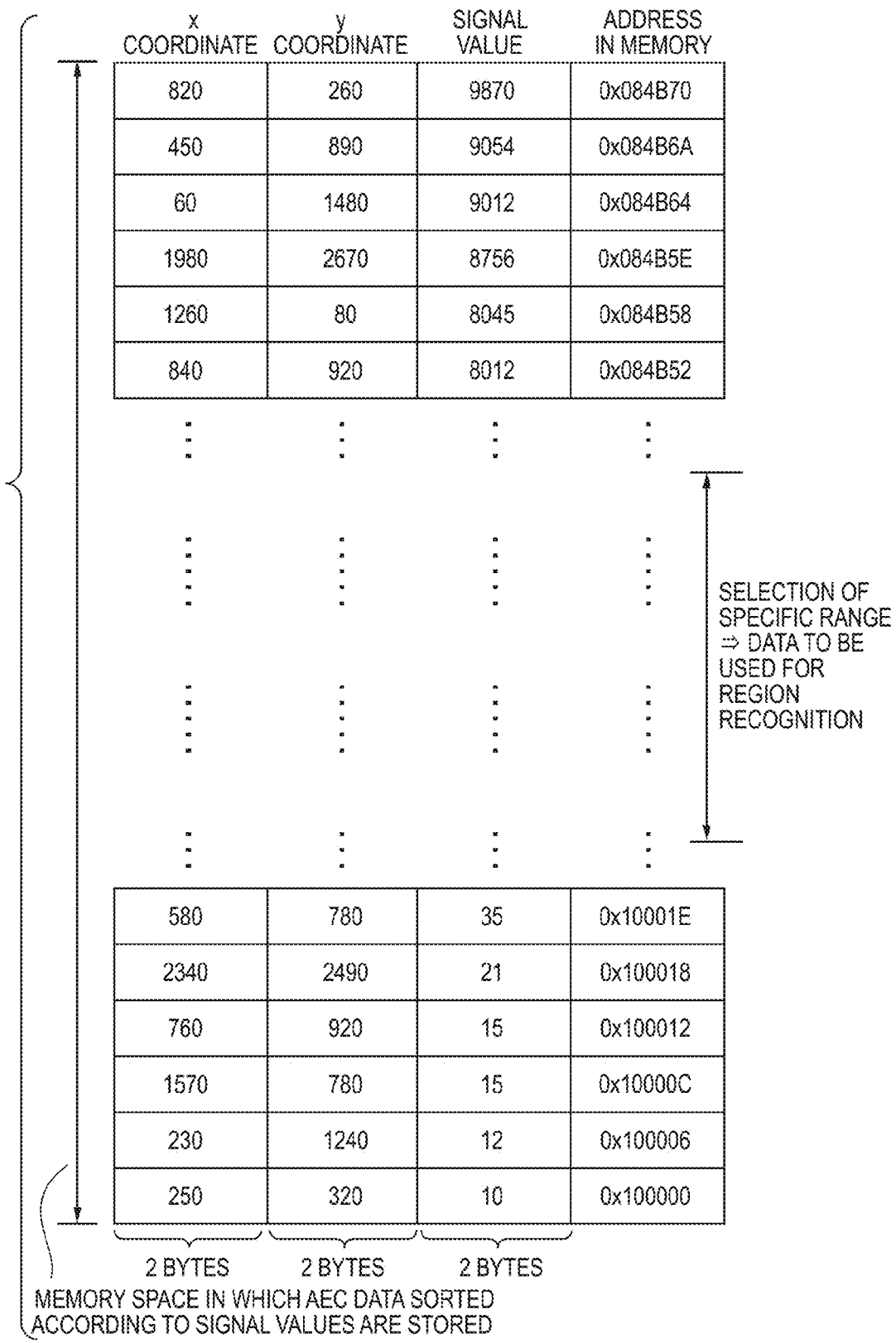
FIG. 10 is a view exemplarily showing sorted signal values.

When signal values sorted in ascending order of signal values and position information are stored in the memory 106d, a histogram of the signal values can be easily generated. FIG. 10 shows a state in which signal values are sorted in descending order of signal values in the memory 106d, while the sensor 212 has 301×301 pixels, and each memory space is provided with two bytes for a signal value and two bytes for each of positions in the x direction and the y direction. The information processing unit 106 sequentially reads out signal values from addresses (0x100000), and the frequencies of signal values are counted for the respective classes.

Figures 11A, 11B:
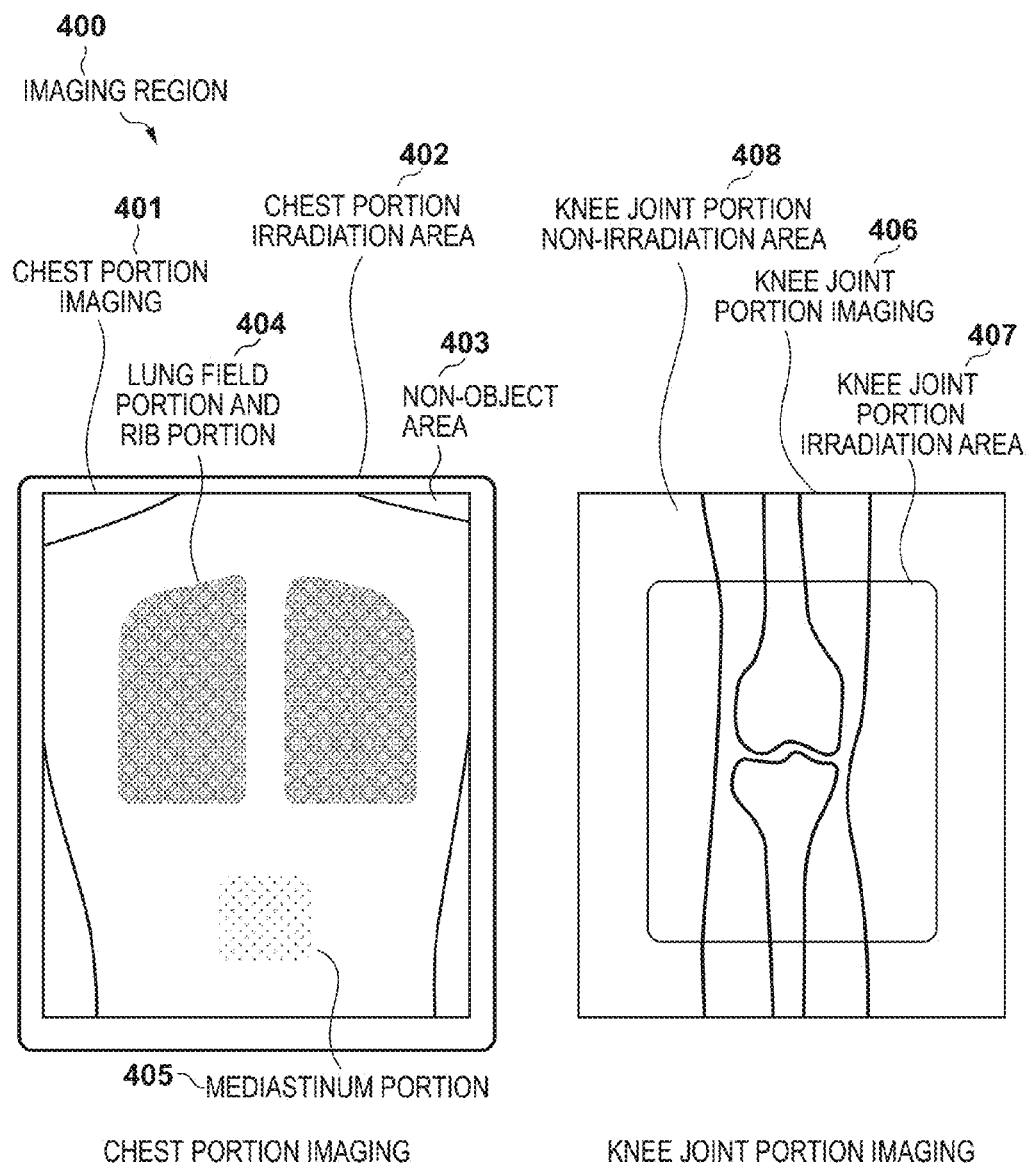
FIGS. 11A and 11B are views exemplarily showing chest portion imaging and knee join portion imaging.
Figure 12:
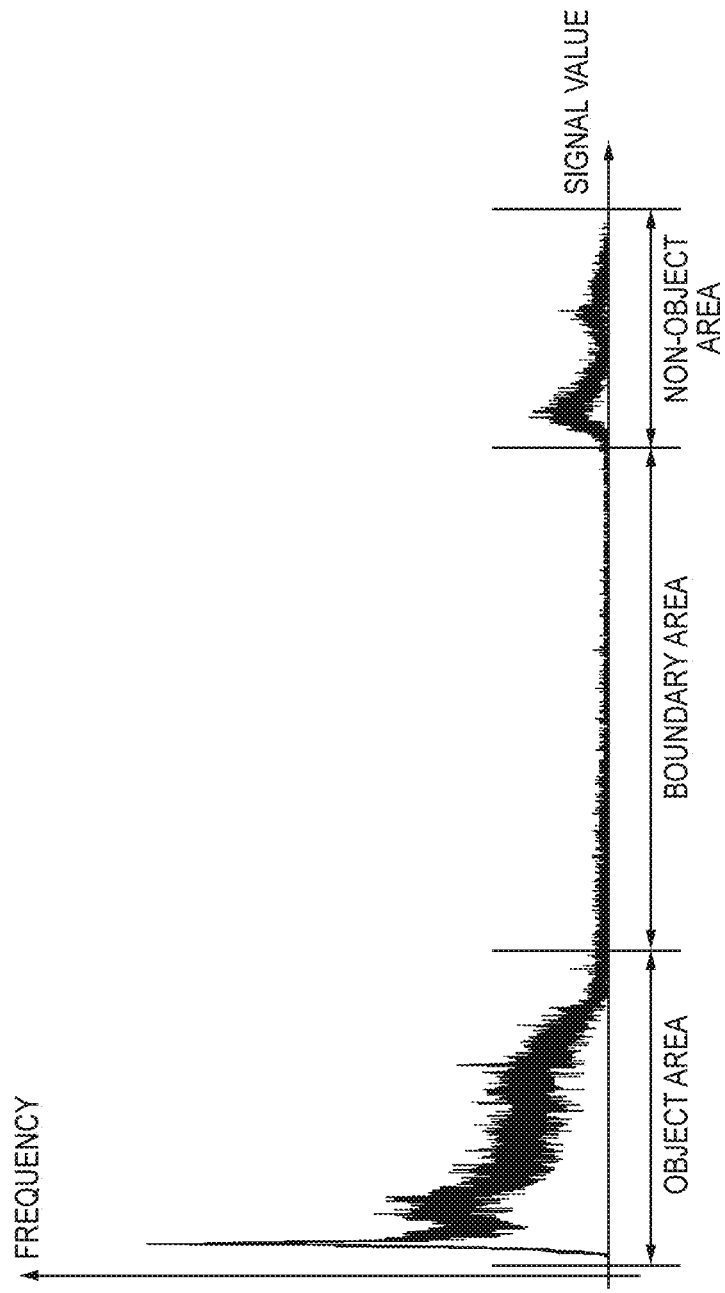
FIG. 12 is a view exemplarily showing a histogram of the signals detected by sensors at the time of chest portion imaging.
Figure 13:
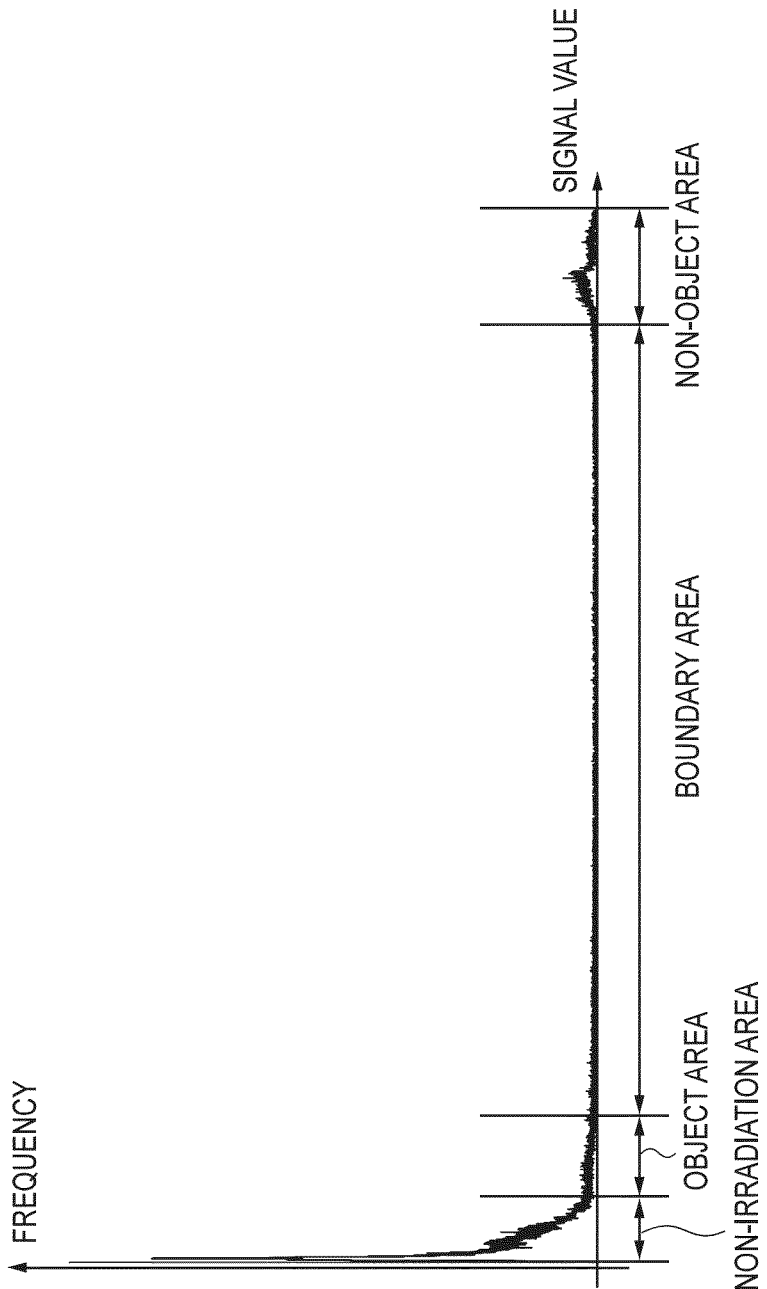
FIG. 13 is a view exemplarily showing a histogram of the signals detected by sensors at the time of knee joint portion imaging.

FIG. 12 exemplarily shows a histogram of the signals detected by the sensors 212 at the time of chest portion imaging shown in FIG. 11A. FIG. 13 exemplarily shows a histogram of the signals detected by the sensors 212 at the time of knee joint portion imaging shown in FIG. 11B. It is obvious that signals in a non-object area and a non-irradiation area can be easily removed based on the shape characteristic of a histogram. Referring to FIG. 12, the histogram has two peaks. An area having the peak on the large signal value side is a non-object area, an area having the peak on the small signal value side is an object area, and an area between the non-object area and the object area is a boundary area. This boundary area greatly depends on the physical features (sex, age, chest circumference, and the like) of the patient (object). As disclosed in Japanese Patent Laid-Open No. 2013-176544, even execution of AEC determination in an area including the maximum value after the removal of a non-object area by a predetermined algorithm is likely to monitor a boundary area. Referring to FIG. 13, an area having the minimum signal value is a non-irradiation area, and an object area, a boundary area, and a non-object area are located on the right side of the non-irradiation area.

In step S306, the monitoring unit 106b determines, as effective sensor candidates, of the plurality of sensors 212 selected in step S301, which exclude the sensors 212 arranged in the non-object area and the non-irradiation area determined by step S305. In addition, the monitoring unit 106b determines monitoring conditions matching information (patient information, imaging region information, and AEC information), of the plurality of monitoring conditions registered in the database 106c, which are set for obtaining a radiation image. The monitoring unit 106b then determines effective sensors from the effective sensor candidates based on the monitoring conditions. In this case, all the monitoring conditions registered in the database 106c are stipulated to determine, as effective sensors, effective sensor candidates, of the plurality of effective sensors, which exclude an effective sensor candidate which has detected a signal having the minimum value and an effective sensor candidate which has detected a signal having the maximum value. In step S306, the monitoring unit 106b determines whether the irradiation dose of radiation has reached the threshold, based on the signals detected by the sensors 212, of the plurality of sensors 212 selected in step S301, which are determined effective sensors. More specifically, in step S306, the monitoring unit 106b determines whether the integrated value of the values of the signals detected by the sensors 212 determined as effective sensors has reached the threshold. Upon determining that the integrated value has reached the threshold, the monitoring unit 106b notifies the radiation source controller 102 and the radiation detection unit 105 of the corresponding information in step S307. In response to this notification, the radiation source controller 102 issues an instruction to stop the emission of radiation to the radiation source 103. In response to this instruction, the radiation source 103 stops the emission of radiation. In addition, the radiation detection unit 105 sequentially reads out signals from the pixels 200 to obtain a radiation image, and transmits the signals to the information processing unit 106. The information processing unit 106 stores the radiation image generated based on the signals from the radiation detection unit 105 in the memory 106d, and causes the input/output device 107 to display the image. In contrast to this, if it is determined that the integrated value has not reached the threshold, the process returns to step S304.

Figure 14:
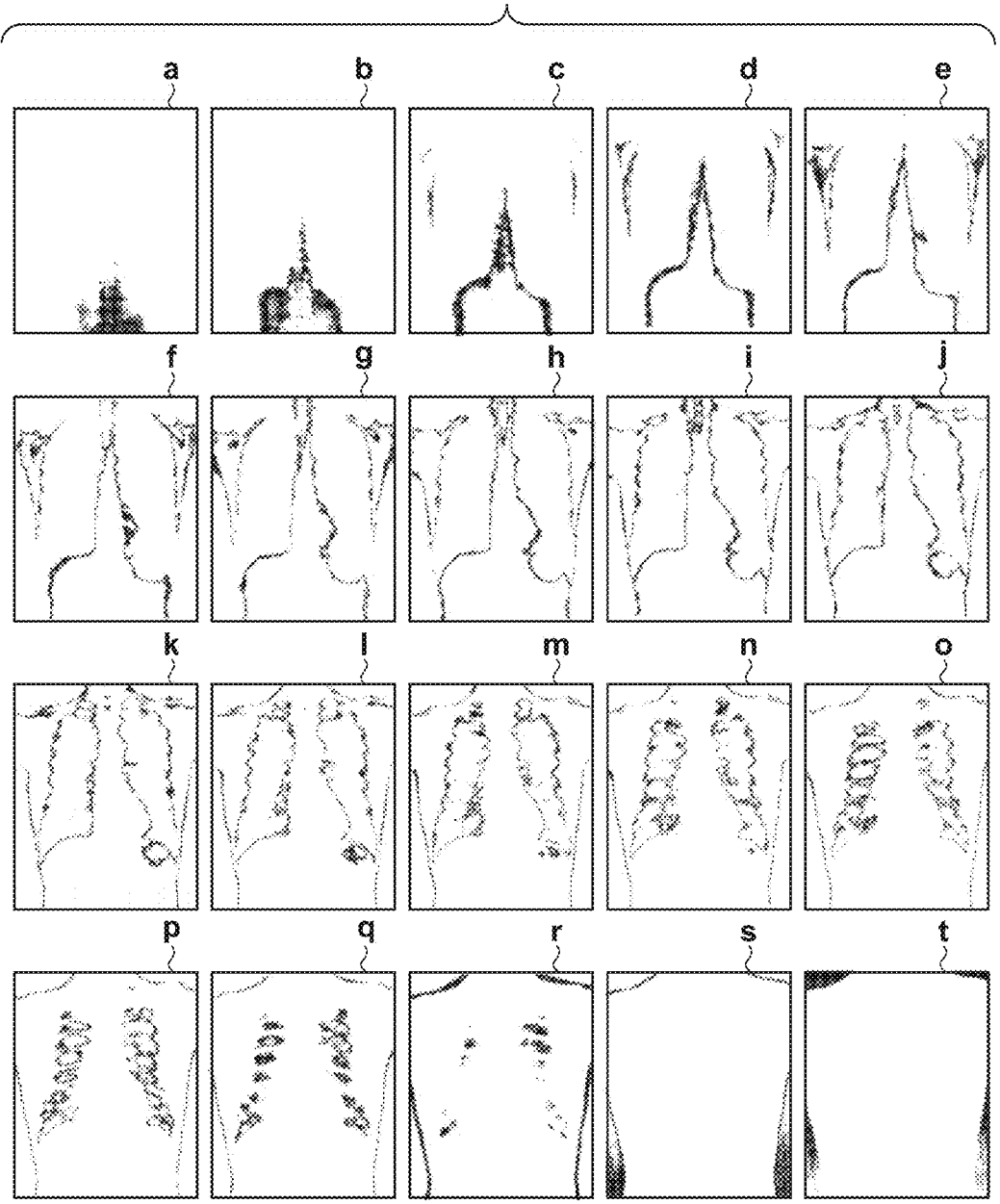
FIG. 14 is a view showing the images obtained by dividing the signals detected by sensors at the time of chest portion imaging according to classes.
Figure 16:
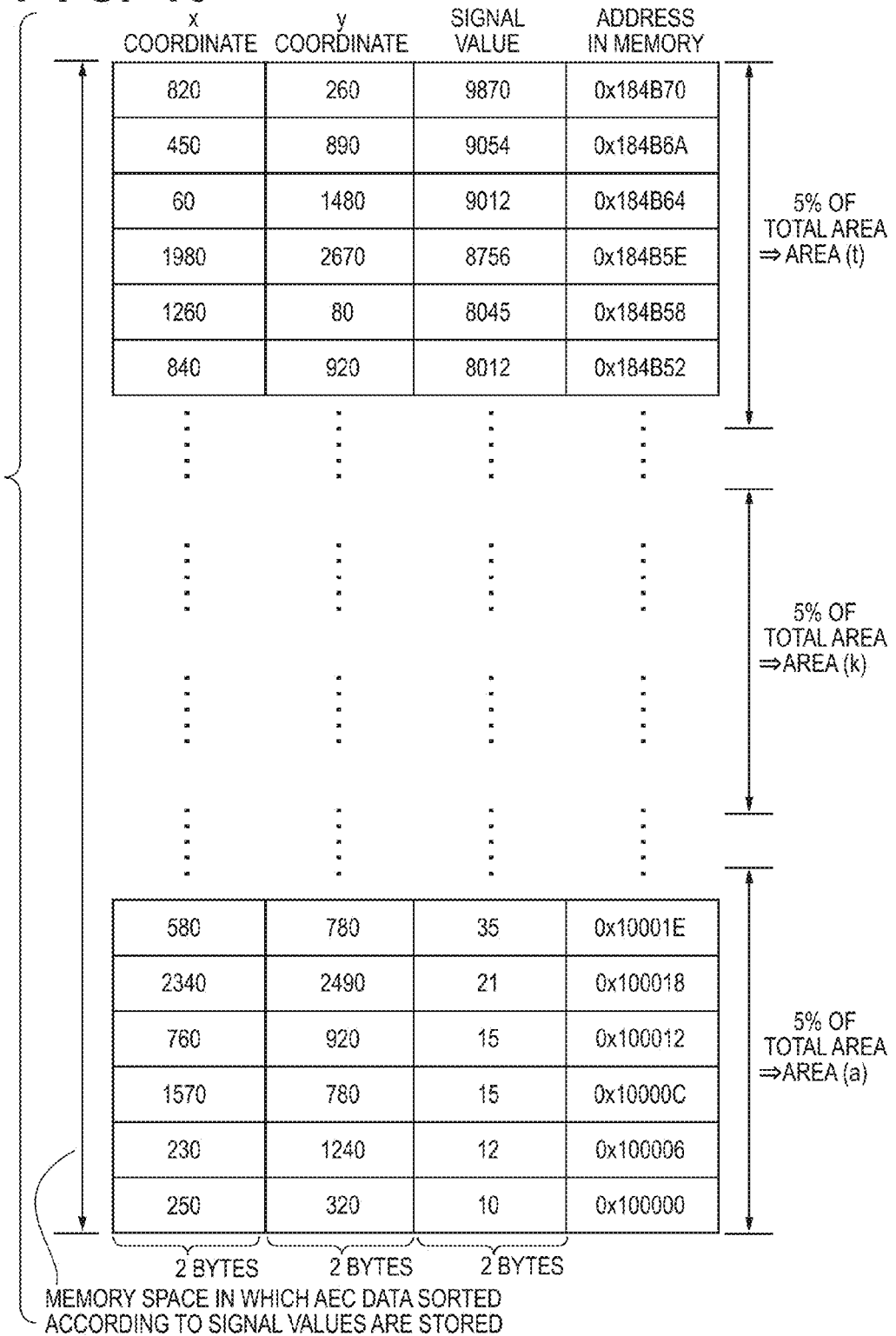
FIG. 16 is a view exemplarily showing the result obtained by sorting signal values.

Referring to FIG. 14, the signals detected by the effective sensor candidates at the time of chest portion imaging are classified to 20 classes in accordance with their values as exemplarily shown in FIG. 16, and the values of the signals in the respective classes are imaged and displayed. When imaging the values of the signals, pixels belonging to the respective classes are expressed as black pixels, and the remaining pixels are expressed as while pixels. The black pixels in (t) and (s) in FIG. 14 represent non-object areas. In addition, in (t) in FIG. 14, black pixels are densely packed on the upper side, whereas in (s) in FIG. 14, black pixels are densely packed on the lower side. This is because the radiation 104 emitted from the radiation source 103 has a spatial distribution, and differs in signal value even in the same non-object area. Such a spatial distribution of radiation becomes a cause of a deterioration in AEC accuracy in the conventional scheme. The black pixels in (r) in FIG. 14 represents the boundary areas between the object and the non-object areas. The presence of such boundary areas means that in the conventional scheme of removing signals in a non-object area by a proper method and using a signal having the maximum value among the remaining signals for AEC, the signal is not guaranteed to be a signal in a region which should be used for AEC.

Figure 15:
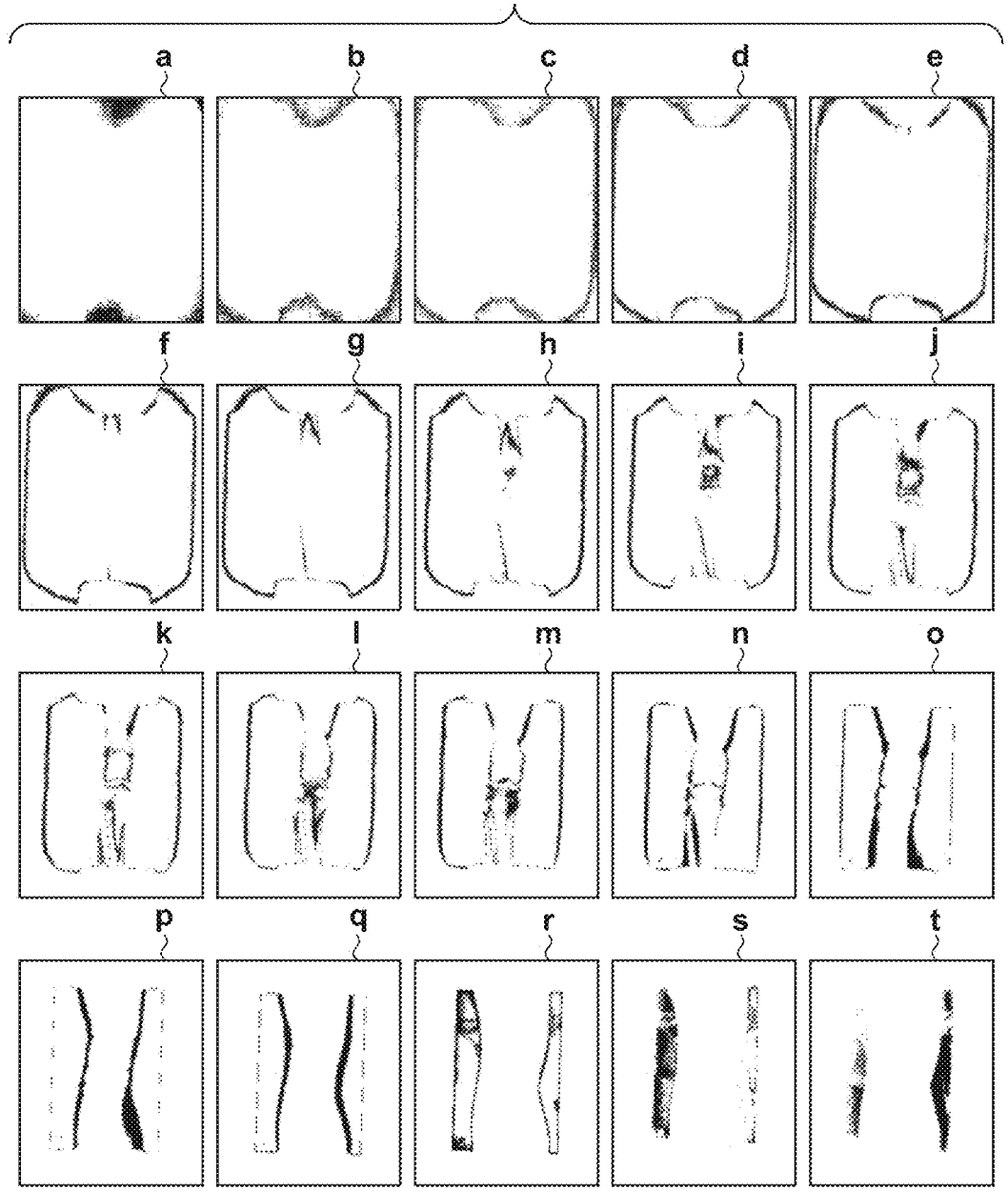
FIG. 15 is a view showing the images obtained by dividing the signals detected by sensors at the time of knee joint portion imaging according to classes.

Referring to FIG. 15, the signals detected by the effective sensor candidates at the time of knee joint portion imaging are classified to 20 classes in accordance with their values as exemplarily shown in FIG. 16, and the values of the signals in the respective classes are imaged and displayed. When imaging the values of the signals, pixels belonging to the respective classes are expressed as black pixels, and the remaining pixels are expressed as while pixels. The black pixels in (t) and (s) in FIG. 15 represent non-object areas. In addition, in (t) in FIG. 15, black pixels are densely packed on the right side, whereas in (s) in FIG. 15, black pixels are densely packed on the left side. This is because the radiation 104 emitted from the radiation source 103 has a spatial distribution. The black pixels in (n) to (r) in FIG. 15 represent the boundary areas between the object and the non-object areas. The black pixels in (h) to (m) in FIG. 15 represent bone portions of the knee joint portion. The black pixels in (a) to (g) in FIG. 15 represent the boundary areas between the non-irradiation areas and the remaining areas. It is obvious from FIGS. 14 and 15 that when the signals detected by effective sensor candidates are classified to a plurality of classes in accordance with their values, specific classes correspond to specific regions.

Figure 17:
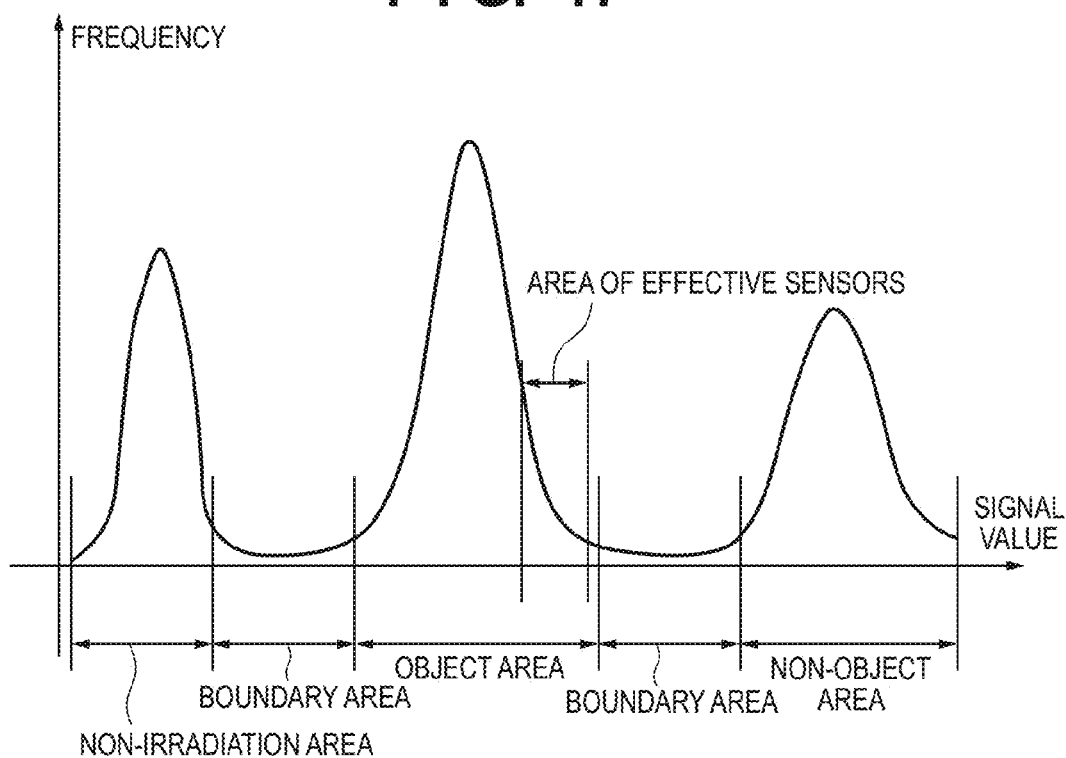
FIG. 17 is a view exemplarily showing a histogram.
Figure 18:
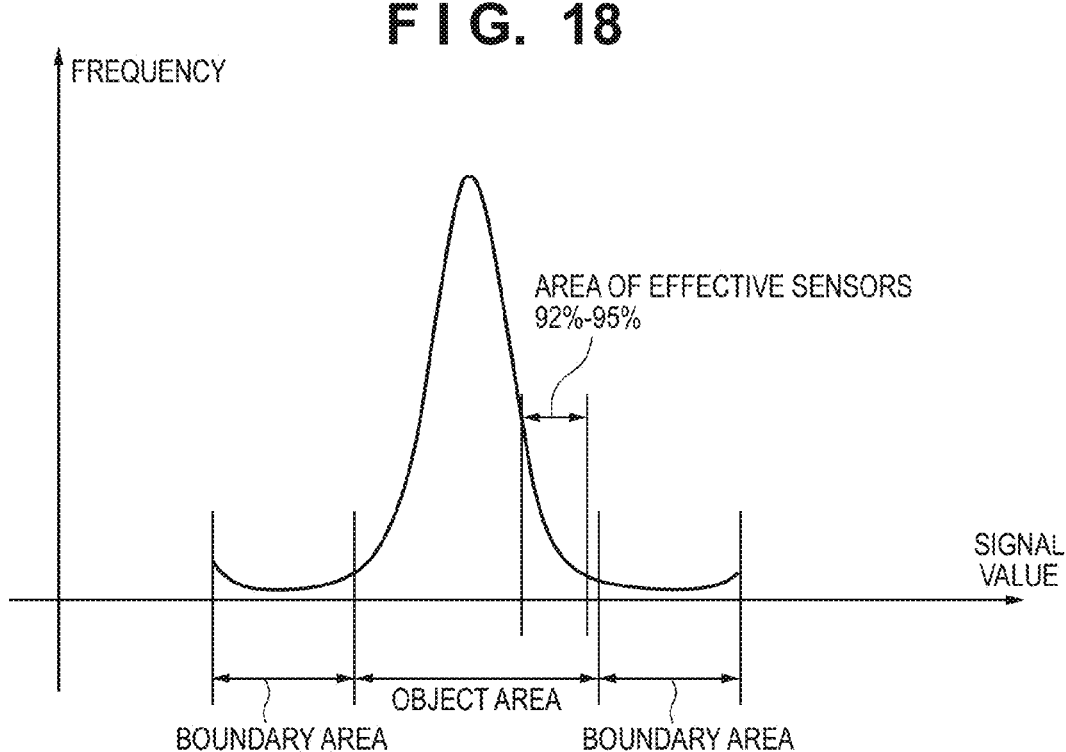
FIG. 18 is a view exemplarily showing a processed histogram.

FIG. 17 exemplarily shows a histogram including a non-irradiation area, an object area, and a non-object area. FIG. 19 exemplarily shows AEC data corresponding to FIG. 17. Boundary areas exist between the non-irradiation area and the object area and between the object area and the non-object area. The monitoring unit 106b deletes the signals in the non-object area and the non-irradiation area from the memory 106d or excludes them from monitoring targets. As a result, as shown in FIG. 18, a histogram is generated, from which the non-object area and the non-irradiation area are excluded. The monitoring unit 106b designates the range of a specific region (the range of signal values from effective sensors) from the histogram shown in FIG. 18, and can calculate the average of signal values in the range. The monitoring unit 106b can issue a request to stop the emission of radiation to the radiation source controller 102 in response to when this average value exceeds a threshold designated in advance. Thereafter, the radiation source controller 102 can stop the emission of radiation by issuing a radiation stop instruction to the radiation source 103.

The radiation imaging apparatus disclosed in Japanese Patent Laid-Open No. 2013-176544 stops the emission of radiation based on the integrated pixel values of the minimum value pixel and the maximum value pixel in an object area. However, since an object area can include various region areas of the object, there is possibility that accurate exposure control cannot be performed for an examination target region by using the scheme of stopping the emission of radiation based on the integrated pixel values of the minimum value pixel and the maximum value pixel in an object area.

The second embodiment of the present invention exemplarily described below provides a technique advantageous in performing correct exposure control on an examination target region. Note that matters not mentioned in the second embodiment can comply with those in the first embodiment.

The arrangement of a radiation imaging system 100 according to the first embodiment of the present invention will be described with reference to FIG. 2. The radiation imaging system 100 includes an emission switch 101, a radiation source controller 102, a radiation source 103, a radiation detection unit 105, an information processing unit 106, and an input/output device 107. The emission switch 101 is a switch which is connected to the radiation source controller 102 via a wired cable or wirelessly and used to issue an instruction to obtain a radiation image (to emit radiation 104 from the radiation source 103 and obtain a radiation image by using the radiation detection unit 105).

The radiation source controller 102 is connected to the emission switch 101, the radiation source 103, and the information processing unit 106, and controls the radiation source 103. The radiation source controller 102 causes the radiation source 103 to emit the radiation 104 (irradiate a patient 108) in response to the signal transmitted from the emission switch 101. The information processing unit 106 is connected to the input/output device 107 and the radiation detection unit 105 and causes the radiation source controller 102 to stop the emission of radiation in response to a signal from the radiation detection unit 105. That is, the information processing unit 106 performs an AEC operation. In addition, the information processing unit 106 causes the input/output device 107 to display the radiation image generated based on a signal from the radiation detection unit 105.

Figure 21:
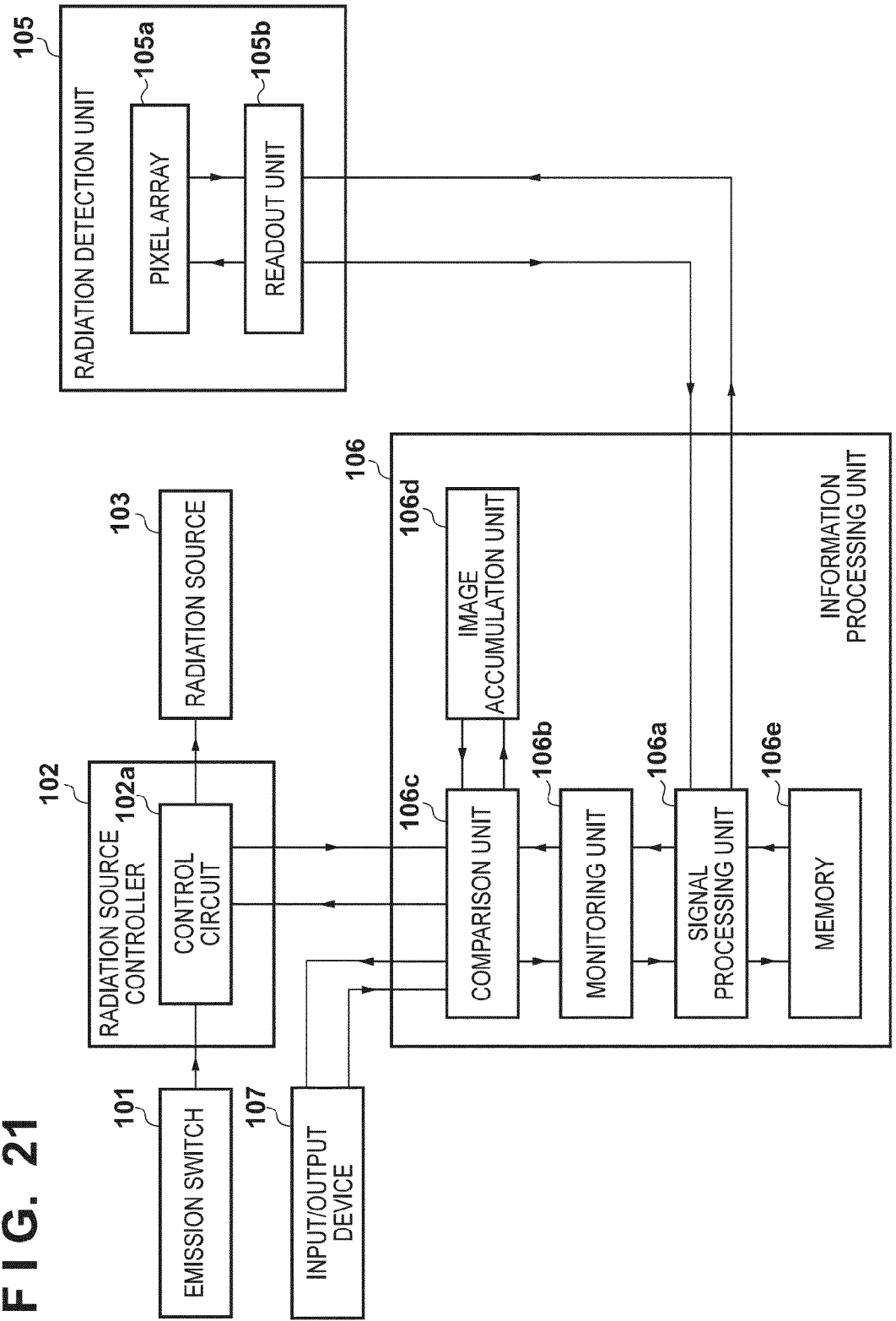
FIG. 21 is a block diagram showing the concrete arrangement of the embodiment of the present invention.

The description will be continued with reference to FIG. 21. The radiation source controller 102 includes a control circuit 102a which controls the radiation source 103. The information processing unit 106 includes a signal processing unit 106a, a monitoring unit 106b, a comparison unit 106c, an image accumulation unit 106d, and a memory 106e, and performs an AEC operation. The information processing unit 106 can be formed by installing programs in a general-purpose computer. Alternatively, the information processing unit 106 can be formed as a device including the signal processing unit 106a formed by installing programs in a general-purpose computer, the monitoring unit 106b formed by installing programs in a general-purpose computer, and the comparison unit 106c formed by installed programs in a general-purpose computer. Such programs or a memory medium storing the programs can also constitute the present invention. Alternatively, the information processing unit 106 can be implemented by a circuit designed or programmed to implement the function (for example, an ASIC (Application Specific Integrated Circuit) or PLD (Programmable Logic Device). Alternatively, the monitoring unit 106b and the signal processing unit 106a constituting the information processing unit 106 each can be implemented by a circuit designed to implement the corresponding function (for example, an ASIC or PLD).

Figure 20:
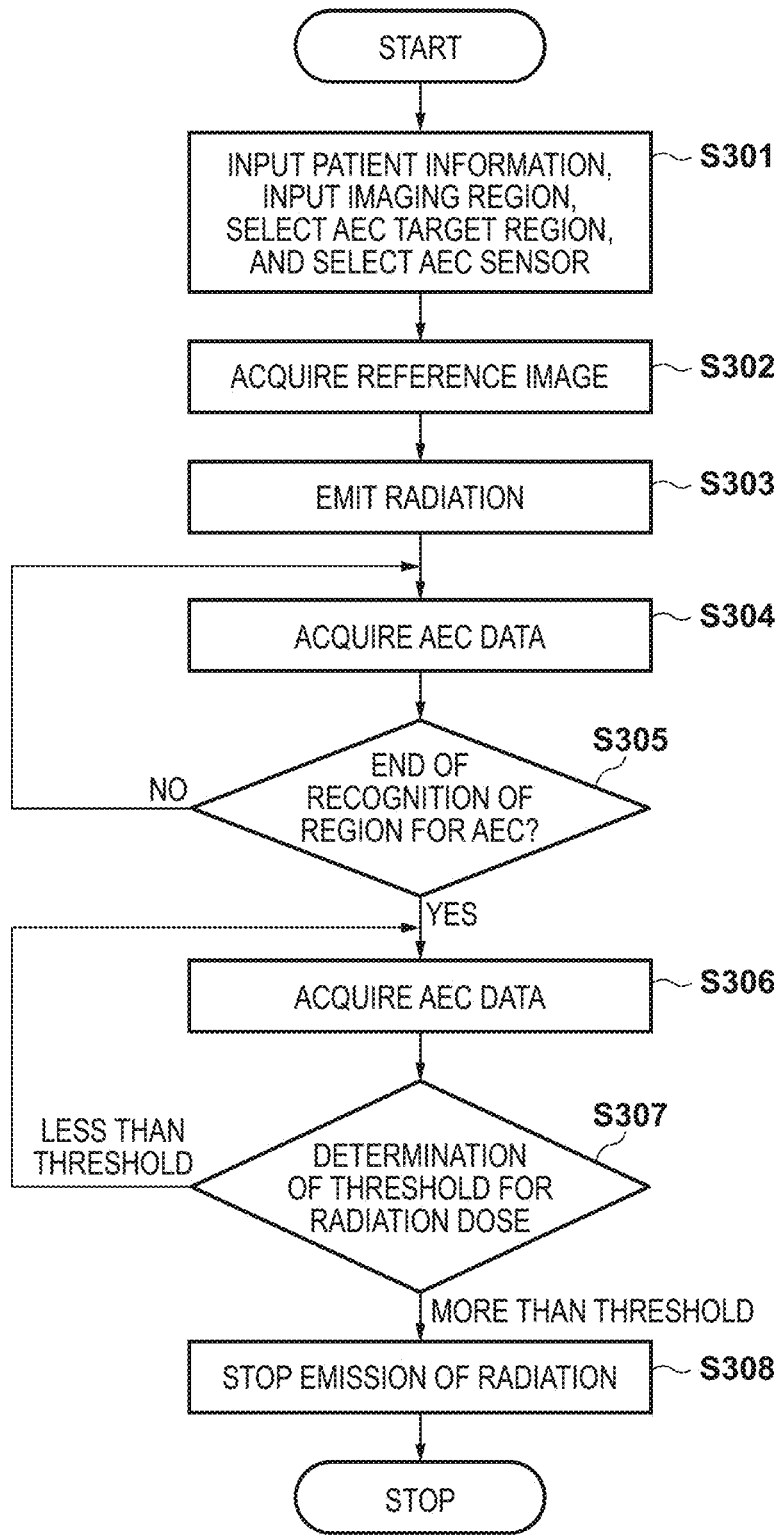
FIG. 20 is a flowchart showing an AEC operation according to the embodiment of the present invention.
Figure 22A:
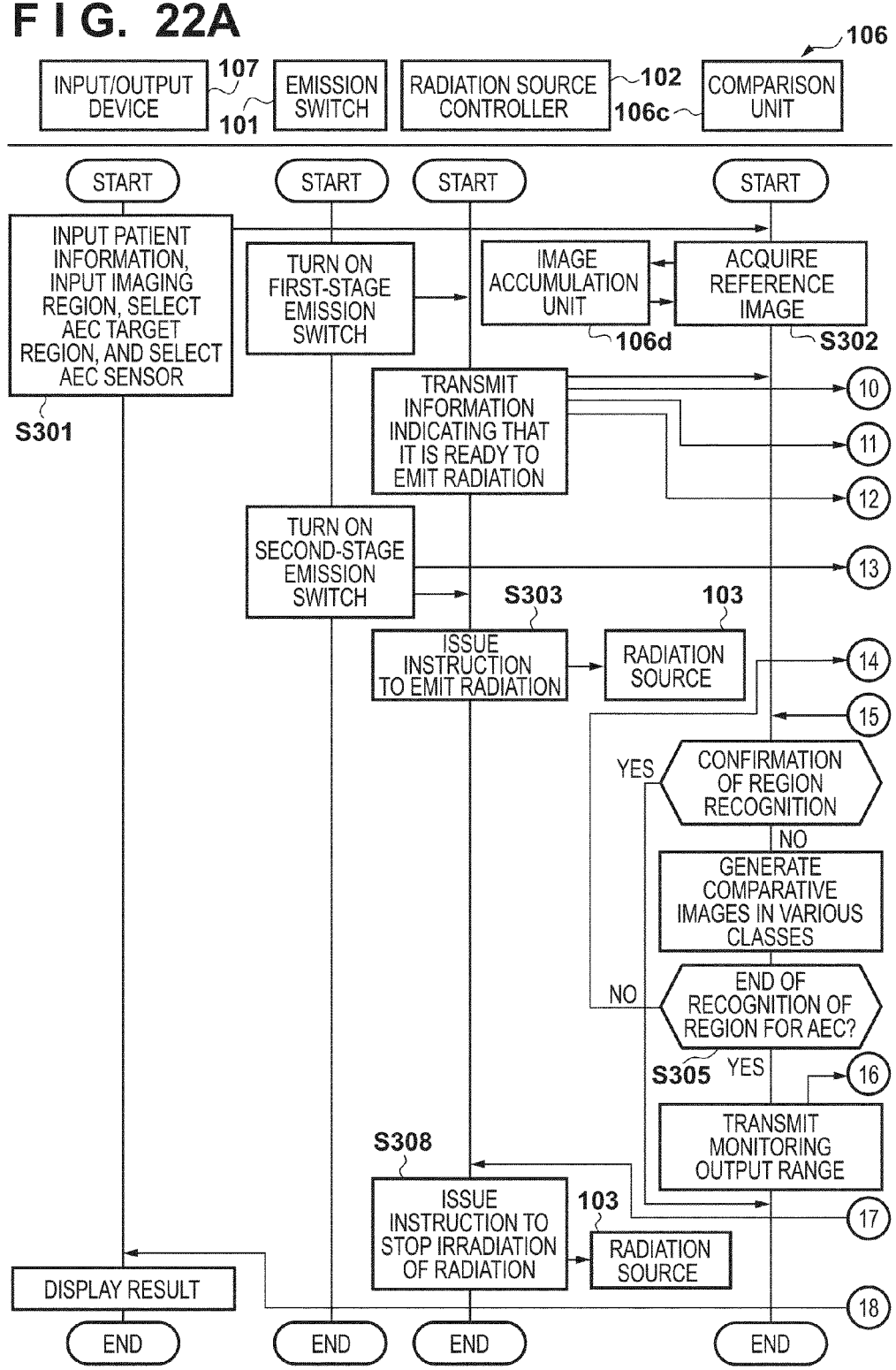
FIGS. 22A and 22B are views showing the operation of the radiation imaging system according to the embodiment of the present invention.
Figure 22B:
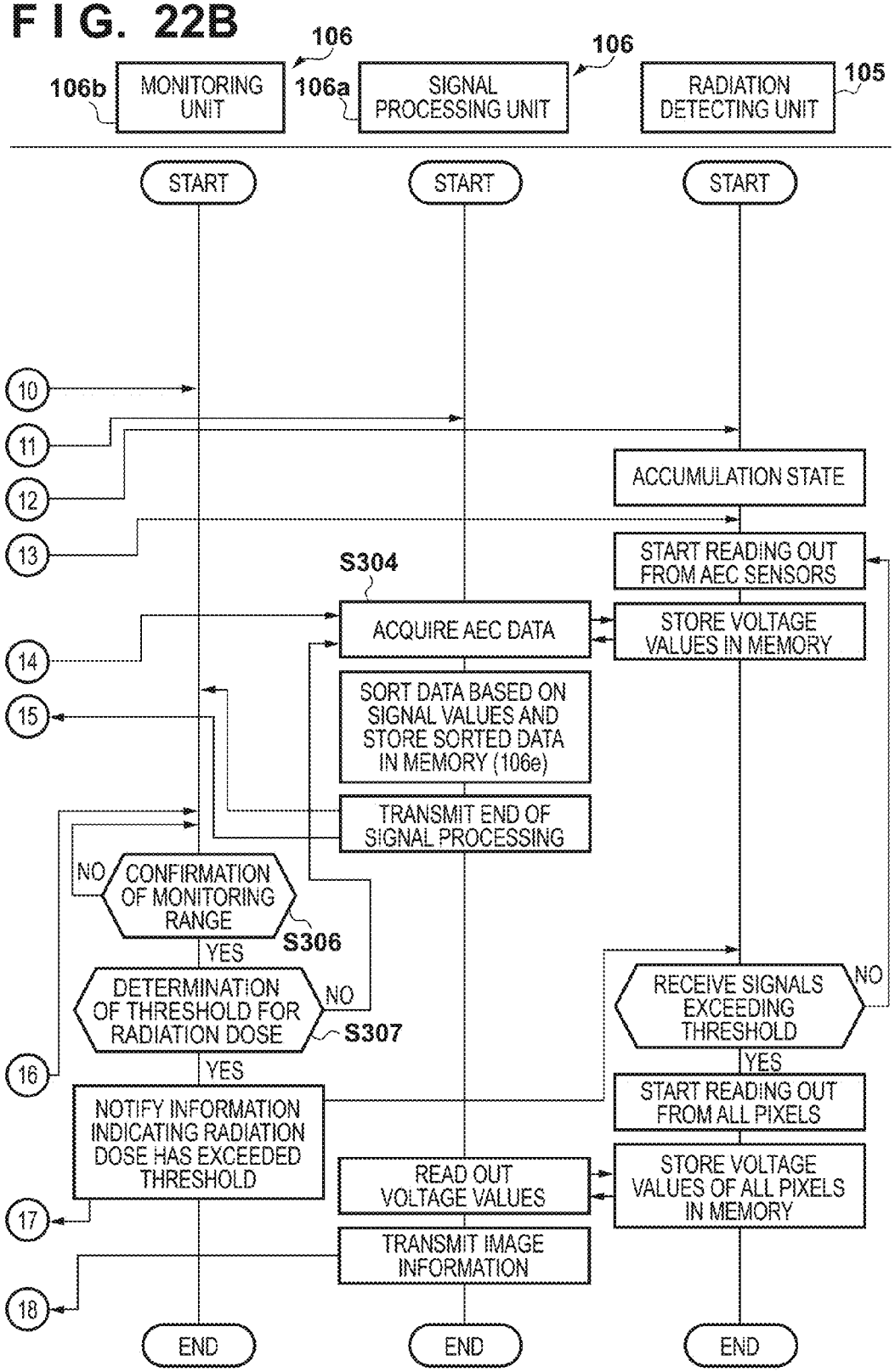

The monitoring unit 106b is connected to the signal processing unit 106a and the comparison unit 106c. The comparison unit 106c is connected to the image accumulation unit 106d. The signal processing unit 106a is connected to the memory 106e. The radiation detection unit 105 includes a pixel array 105a and a readout unit 105b. The pixel array 105a is a device including a plurality of sensors which detect radiation. The plurality of sensors may be used as pixels for obtaining radiation images or may dedicated sensors for detecting radiation. The readout unit 105b reads out signals from the pixel array 105a and outputs them to the information processing unit 106. The signal processing unit 106a can include a function of sorting, for example, the signals output from the radiation detection unit 105 based on their values. Referring to FIG. 21, although the comparison unit 106c is not directly connected to the signal processing unit 106a, they can transmit/receive data to/from each other via the monitoring unit 106b. Likewise, the comparison unit 106c and the memory 106e can transmit/receive data to/from each other, and so do the monitoring unit 106b and memory 106e The operation of the radiation imaging system 100 will be described below with reference to FIGS. 20 and 22. Note that FIGS. 22A and 22B show the operations of the input/ output device 107, the emission switch 101, the radiation source controller 102, the information processing unit 106, and the radiation detection unit 105 in correspondence with each step in the flowchart of FIG. 20.

In step S301, the doctor or radiation technician provides patient information (object information) to the information processing unit 106 via the input/output device 107. Patient information is, for example, information characterizing an object such as sex, age, weight, chest circumference, and abdominal circumference. More specifically, patient information can be, for example, sex: male, weight: 70 kg, chest circumference: 100 cm, and abdominal circumference: 80 cm. In step S301, the doctor or radiation technician provides imaging region information indicating an imaging region via the input/output device 107. An imaging region is, for example, a head portion, chest portion, or abdominal portion.

In step S301, the input/output device 107 provides information designating an AEC target region used for AEC and pixels 200 as sensors 212 for AEC to the information processing unit 106. If, for example, an imaging region is a chest portion, an AEC target region is set as a lung field portion, the pixels 200 arranged at intervals of 1 mm to 1 cm in the x direction and the y direction are selected as sensors 212, as exemplarily shown in FIG. 6. Note that if the pixel size is about 150 μm×150 μm, pixels arranged at intervals 1 mm to 1 cm correspond to pixels arranged at intervals of 8 pixels to 80 pixels. In this case, μm indicates micrometer. An AEC target region and the sensors 212 may be selected by the input/output device 107 in accordance with an imaging region or may be selected by the doctor or radiation technician. For example, the input/output device 107 can set an AEC target region and the sensors 212 as defaults. The doctor or radiation technician can change the default AEC target region and the default sensors 212, as needed. Information designating an AEC target region and the sensors 212 is an example of AEC information.

In the case shown in FIG. 6, the sensors 212 are set for every multiple of k, like the kth row, the (2×k)th row, . . . , the interval between the adjacent sensors 212 is set to about 1 mm to 1 cm. However, this is merely an example. It is possible to arbitrarily select sensors 212 from the plurality of pixels 200 constituting the pixel array 105a in accordance with an AEC target region. If, for example, an AEC target region is a lung field portion, the pixels 200 arranged at intervals equal to or less than the size of the lung field portion are preferably determined as the sensors 212. This makes at least one sensor 212 be located within the area of the AEC target region. The input/output device transmits patient information, imaging region information, and AEC information to the comparison unit 106c of the information processing unit 106.

In step S302, the comparison unit 106c acquires a reference image corresponding to the information (patient information, imaging region information, and AEC information) provided in step S301 from the image accumulation unit 106d. In this case, in the image accumulation unit 106d, one reference image is associated with each of a plurality of combinations of information each including patient information, imaging region information, and AEC information. Therefore, specifying patient information, imaging region information, and AEC information can specify one reference image corresponding to them. The form of reference images accumulated in the image accumulation unit 106d can be arbitrary. For example, a binary image like that shown in FIG. 23B can be used. A binary image can be constituted by black pixels representing an examination target (for example, a lung field portion) and white pixels representing the remaining area. FIG. 23A shows an example of a radiation image of a chest portion which is expressed by an 8-bit grayscale. FIG. 23B shows the binary image obtained by extracting the lung field portion from the image shown in FIG. 23A and expressing the lung field portion by black pixels while expressing the remaining area by white pixels.

The pixels constituting a reference image may include the pixels 200 used as the sensors 212 or the pixels 200 near the pixels 200 used as the sensor 212. For example, in the case of the pixel array 105a having 3,000 pixels in the x direction and 3,000 pixels in the y direction, it is not necessary to form a reference image by using all the data corresponding to 3000×3000=9,000,000 pixels. A reference image may include at least the pixels at the coordinates of all the sensors 212. Consider a case in which pixels at a coordinate 0 in the x direction and a coordinate of 0 in the y direction and every 10th pixels in x direction and the y direction are designated as the sensors 212. In this case, the data constituting a reference image can include pixels at a coordinate of 0 in the x direction, a pixel at a coordinate of 0 in the y direction, every pixels, every second pixels, every five pixels, or every 10th pixels in the x direction, and every pixels, every second pixels, every five pixels, or every 10th pixels in the y direction.

Using a binary image as a reference image is advantageous in reducing the file size. In the pixel array 105a having 3,000 pixels arrayed in the x direction and 3,000 pixels arrayed in the y direction, when the data of each pixel is expressed in 8 bits, that is, 1 byte, 3000×3000×1=9,000,000 bytes. However, if the sensors 212 are designated at intervals of 10 pixels in the x direction and the y direction, and 8-pixel information can be stored in a 1-byte memory space, with 1 pixel corresponding to 1-bit information, 3000×3000×0.1×0.1÷8=11 kB (kilobytes). More accurately, since the coordinate information of each pixel is required, information concerning the width of the interval between pixels and coordinate information of one pixel are required. The actual size is slightly larger than the above size. Such information may be written in the head portion of image data. In addition, if the information included in a binary image is randomly stored instead of at intervals of a given number of pixels, since coordinate information is required for all the output values. This further increases the file size.

There are two advantages when using a binary image with a small file size as a reference image. The first advantage is that the region determination speed can be increased by reducing the file size of a reference image. The second advantage is that it is possible to easily form a region specifying algorithm.

In step S303, the radiation source 103 is ready to emit the radiation 104. The doctor or radiation technician operates the emission switch 101 to emit radiation from the radiation source 103 and irradiate the patient 108 with the radiation. In general, the emission switch 101 is a two-stage switch. When the first-stage switch is turned on, the radiation source 103 starts a preliminary operation. This preliminary operation is an operation necessary for stable emission of the radiation 104. When the second-stage switch is turned on, the radiation 104 is emitted from the radiation source 103. As shown in FIGS. 22A and 22B, when the first-stage switch of the emission switch 101 is turned on, information indicating that the radiation source 103 has started a preliminary operation is transmitted to the monitoring unit 106b, the signal processing unit 106a, and the radiation detection unit 105.

The readout unit 105b of the radiation detection unit 105 causes the pixels 200 including the sensors 212 to start accumulating charges in response to the turning on of the first-stage switch of the emission switch 101. Thereafter, when the second-stage switch of the emission switch 101 is turned on to emit the radiation 104 from the radiation source 103, the readout unit 105b of the radiation detection unit 105 starts a readout operation for the signals detected by the sensors 212.

In step S304, the signal processing unit 106a of the information processing unit 106 acquires the signals detected by the sensors 212, that is, AEC data. FIG. 8 shows a readout operation for signals (detected by the sensors 212) corresponding to the charges accumulated in the sensors 212 of the pixel array 105a. The readout operation is performed with respect to only the AEC sensors 212 of the pixels 200 constituting the pixel array 105a. More specifically, driving lines 205 on rows defined by multiples of k, like the kth row, the (2×k)th row, the (3×k)th row, . . . , are sequentially driven to an active level in accordance with the coordinates of the sensors 212 shown in FIG. 6. The potential of the remaining driving lines 205 is maintained at an inactive level.

First, the signals detected by the sensors 212 on the kth row are read out. An amplification units 207 are reset. Thereafter, a driving unit 206 drives the driving line 205 on the kth row to an active level to turn on the switches 203 of the sensors 212 on the kth row. When the switches 203 are turned on, the charges accumulated in the conversion elements 202 are transferred to the amplification units 207. A sample/hold circuit (not shown) samples/holds the signals obtained by causing the amplification units 207 to convert charges into analog voltage values D1, D2, D3, . . . . The multiplexer 208 sequentially transmits the signals detected by the sensors 212 on the kth row to the ADC 209, which then converts the analog voltage values D1, D2, D3, . . . into digital voltage values D'1, D'2, and D'3, . . . . The multiplexer 208 is only required to output only signals from the sensors 212, and hence select only the columns on which the sensors 212 exist. Referring to FIG. 6, since the sensors 212 exist for every f columns, the multiplexer 208 sequentially selects the fth column, the (2×f)th column, the (3×f)th column, . . . .

The signals (AEC data) read out in this manner are sequentially stored in the memory 211. In this case, the memory 211 stores the signals (the signals detected by the sensors 212) read out from the sensors 212 in correspondence with the coordinate information (position information) of the sensors 212. More specifically, with regard to one sensor 212, a memory space having a total of about six bytes is used: about two bytes for each of positional information in the x direction and positional information in the y direction and about two bytes for the signal read out from the sensor 212 (note that if the resolution of the ADC is 16 bits or more, three bytes or more are used). After a readout operation for the kth row is complete, readout operations are sequentially performed on the (2×k)th row, the (3×k)th row, . . . , and the readout information is stored in the memory 211, together with the positional information of the sensor 212.

Figure 9:
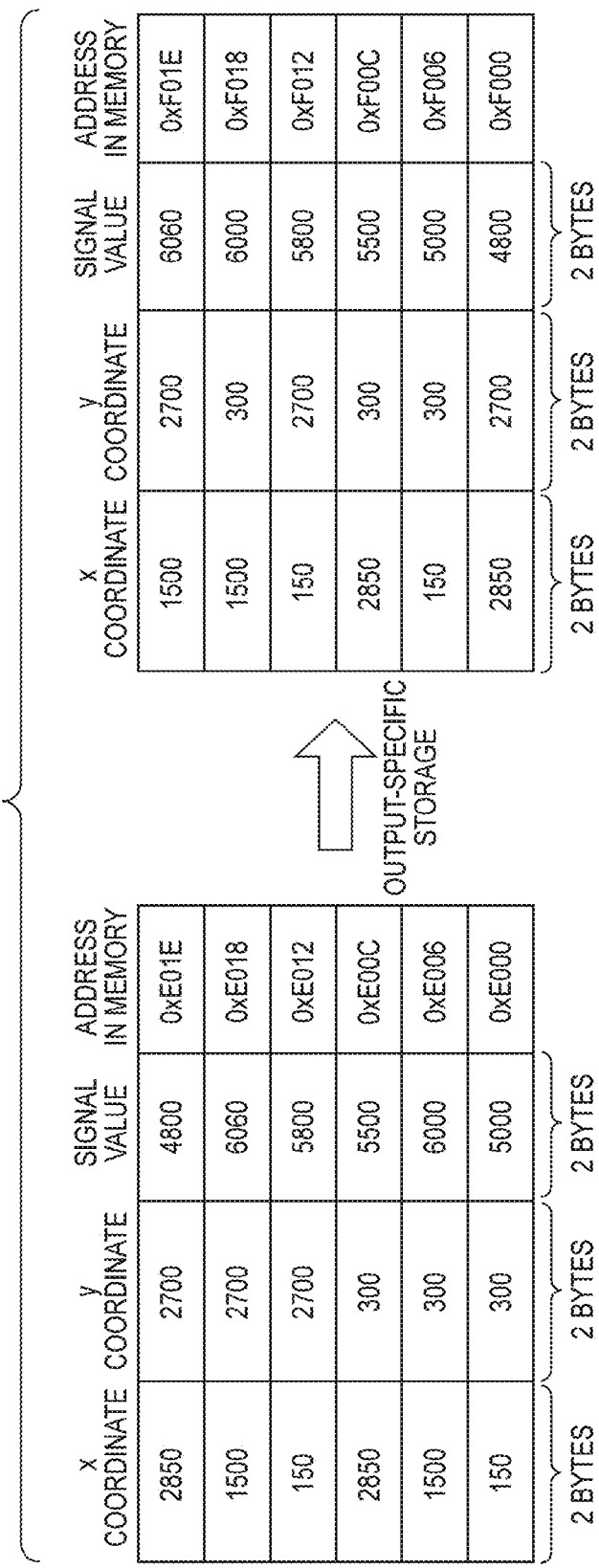
FIG. 9 is a view exemplarily showing the sorting of signal values.

In step S305, a region to be used for AEC is recognized. When the AEC data (the signal value detected by each sensor 212) read out from each sensor 212 is stored in the memory 211, the signal processing unit 106a reads out the signal accumulated in the memory 211 and the coordinate information associated with the signal, and copies them to the memory 106e. As shown in FIG. 9, the signal processing unit 106a then sorts the signals copied to the memory 106e in ascending order of the signal values, and stores the signal values and pieces of coordinate information associated and paired with them in another area of the memory 106e.

In this case, if the AEC data is 5000, the position of the sensor 212 in the x direction is 150, the position of the sensor 212 in the y direction is 300, and the start memory address of the storage destination is 0001, the corresponding information is written as (5000, 150, 300, 0x0001). "Ox" indicates that a memory address is expressed in hexadecimal.

Assume that the following six pieces of information are stored in the memory 106e:
(5000, 150, 300, 0x0000)
(6000, 1500, 300, 0x0006)
(5500, 2850, 300, 0x000C)
(5800, 150, 2700, 0x0012)
(6060, 1500, 2700, 0x0018)
(4800, 2850, 2700, 0x001E)

In this case, the value of each signal can be expressed by two bytes, coordinates are expressed by two bytes, and a memory space of a total of six bytes is used. Since six bytes are used for one sensor 212, the number of memory addresses increases by six per one sensor 212. When these six pieces of information are arranged in ascending order of signal values, these pieces of information are stored in another memory space in the following order:
(4800, 2850, 2700, 0x1000)
(5000, 150, 300, 0x1006)
(5500, 2850, 300, 0x100C)
(5800, 150, 2700, 0x1012)
(6000, 1500, 300, 0x1018)
(6060, 1500, 2700, 0x101E)

This operation is performed for the signals obtained from all the sensors 212 and positional information.

Signals from a plurality of sensors 212 concerning one region are expected to have almost the same value. For example, in the case of lung field portions, signals originating from the right lung field portion and the left lung field portion have almost the same value. That is, as exemplarily shown in FIG. 10, it is possible to obtain AEC data concerning a specific region of an object by extracting a plurality of adjacent AEC data of a series of AEC data sorted according to signal values and stored in the memory 106e. Therefore, comparing the AEC data stored in the memory 106e with the reference image exemplarily shown in FIG. 23B can specify which region the AEC data represents. This indicates that it is possible to specify AEC data corresponding to a region to be examined. It is therefore possible to control exposure with high accuracy in accordance with an examination target region.

In addition, as exemplarily shown in FIG. 16, by equally dividing the AEC data sorted according to signal values and stored in the memory 106e into a plurality of classes, it is possible to equalize the numbers of sensors 212 belonging to the respective classes. The AEC data belonging to each of a plurality of classes (area (t), area (k), and area (a)) exemplarily shown in FIG. 16 is constituted by a set of pairs of signal values and coordinates, and hence can be handled as an image. The AEC data belonging to the respective classes exemplarily shown in FIG. 16 can be handled as images generated in correspondence with the plurality of classes by dividing the signals detected by the sensors 212 to the plurality of classes based on the signal values. In other words, the signal processing unit 106a can generate a plurality of images in correspondence with a plurality of classes by dividing the signal values of the signals detected by a plurality of sensors 212 to the plurality of classes based on the signal values. In this case, when generating each image, signals, of the signals detected by the plurality of sensors 212, which have signal values other than 0 can be expressed as black pixels, and signals, of the signals detected by the plurality of sensors 212, which have a signal value of 0 can be expressed as while pixels.

FIG. 14 shows a plurality of images ((a) to (t) in FIG. 14) respectively corresponding to a plurality of classes a to t based on the signal values of the signals detected by a plurality of sensors 212 at the time of chest portion imaging shown in FIG. 11A. Classes a, b, c, d, . . . , t are respectively a class in which signal values range from 0% to 5%, a class in which signal values range from 5% to 10%, a class in which signal values range from 10% to 15%, a class in which signal values range from 15% to 20%, . . . , a class in which signal values range from 95% to 100%. In FIG. 14, (a) shows a binary image with signal values belonging to class a being black pixels and remaining signal values being white pixels. The image shown in (a) in FIG. 14 will be referred to as a class-a image. In FIG. 14, (b) shows a binary image with signal value belonging to class b being black pixels and remaining signal values being white pixels. The image shown in (b) in FIG. 14 will be referred to as a class-b image. Likewise, (c) to (t) in FIG. 14 respectively show binary images with signal values belonging to classes c to t being black pixels and the remaining signal values being white pixels. In FIG. 14, (a) to (t) each show an example of selecting, as sensors 212, every 10th pixels from the plurality of pixels 200 constituting the pixel array 105a in the x direction and the y direction.

The data obtained by sorting the signals detected by the sensors 212 exemplarily shown in FIG. 16 in descending order of the signal values is advantageous in generating a histogram. FIG. 24 exemplarily shows a histogram of AEC data (the signals detected by the sensors 212). This histogram includes a non-object area, a non-irradiation area, and a boundary area. In this case, the non-object area is an area, of the imaging area formed by the pixel array 105a, which radiation enters without being transmitted through an object. The non-irradiation area is an area, of the imaging area formed by the pixel array 105a, which is not irradiated with radiation. The boundary area is the area between the non-object area and the object area.

In FIG. 14, (t) and (s) show non-object area images. In FIG. 14, (r) shows an image of the boundary area (in this case, an area corresponding to a skin portion) between the non-object area and the object area. This image is an image in an area with high transmissivity. In FIG. 14, (q) shows an image of an area obtained by removing a rib portion in the lung field portion. In FIG. 14, (n) to (p) show images of areas each corresponding to the lung field portion including the rib portion. In FIG. 14, (f) to (c) show images each corresponding to the boundary area between the lung field portion and the remaining portion. In FIG. 14, (a) and (b) each show an image of the mediastinum portion. As described above, it is possible to specify a specific region (for example, the lung field portion) by dividing the signals detected by a plurality of sensors 212 to a plurality of classes.

FIG. 15 shows a case in which a plurality of images ((a) to (t) in FIG. 15) respectively corresponding to a plurality of classes a to t are generated by dividing the signals detected by a plurality of sensors 212 at the time of knee joint portion imaging shown in FIG. 11B to classes a to t based on the signal values. As in the case of FIG. 14, classes a, b, c, d, . . . , t are respectively a class in which signal values range from 0% to 5%, a class in which signal values range from 5% to 10%, a class in which signal values range from 10% to 15%, a class in which signal values range from 15% to 20%, . . . , a class in which signal values range from 95% to 100%. In FIG. 15, (a) shows a binary image with signal value belonging to class a being black pixels and remaining signal values being white pixels. The image shown in (a) in FIG. 15 will be referred to as a class-a image. In FIG. 15, (b) shows a binary image with signal value belonging to class b being black pixels and remaining signal values being white pixels. The image shown in (b) in FIG. 15 will be referred to as a class-b image. Likewise, (c) to (t) in FIG. 15 respectively show binary images with signal values belonging to classes c to t being black pixels and the remaining signal values being white pixels. In FIG. 15, (a) to (t) each show an example of selecting, as sensors 212, every 10th pixels from the plurality of pixels 200 constituting the pixel array 105a in the x direction and the y direction. In FIG. 15, (r) to (t) each show an image of a non-object area. In FIG. 15, (o) to (q) each show an image of the boundary area between the object area and the non-object area. In FIG. 15, (n) and (g) to (k) each show an image of a bone portion. In FIG. 15, (l) and (m) each show an image of a knee joint portion. As is obvious from FIG. 15, it is possible to specify a specific region (for example, a knee joint portion) by dividing the signals detected by a plurality of sensors 212 to a plurality of classes.

In addition, a comparison between (t) and (s) in FIG. 14 reveals that black pixels are densely packed on the upper side in (t) in FIG. 14, whereas black pixels are densely packed on the lower side in (s) in FIG. 14. This is because the radiation 104 emitted from the radiation source 103 has a spatial distribution, and differs in signal value even in the same non-object area. Such a spatial distribution of radiation becomes a cause of a deterioration in AEC accuracy in the conventional scheme. If the radiation 104 is uniform, uniform non-object areas should exist in both the images in (t) and (s) in FIG. 14. In addition, consider (r) in FIG. 14. In this case, although a lung field portion is slightly drawn, the dominant area is the boundary area between the object area and the non-object area. It is difficult to monitor the dose of radiation with high accuracy by the conventional method because radiation has a spatial distribution and an area in which a signal value is second largest to that in a non-object area is mostly the boundary area between the object area and the non-object area.

The comparison unit 106c selects, as a monitoring image, one of a plurality of images stored in the memory 106e in correspondence with the respective classes based on the similarity between each of at least some of the plurality of images and the reference image exemplarily shown in FIG. 23B. A method of determining a monitoring sensor will be described with reference to FIG. 25. Referring to FIG. 25, assume that the memory space in which the AEC data sorted in accordance with signal values (in descending order of signal values) are stored is defined as memory space A. Memory space A is divided into, for example, 20 areas. This operation is equivalent to dividing AEC data to 20 classes according to the signal values. In addition, the comparison unit 106c regards the AEC data in each divided area and coordinate information (x- and y-coordinates) as an image (an image in a class corresponding to each divided area) with coordinates at which signal values exist being black pixels and the remaining coordinates being white pixels, and compares the image with a reference image. The comparison unit 106c then determines the sensors 212 which have detected signals constituting image in a class exhibiting the highest similarity with the reference image as a result of the comparison as monitoring sensor for AEC.

A reference image need not be a binary image as long as it can be compared with an image in each class. The number of divisions (that is, the number of classes) of memory space A need not be 20, and may be, for example, 10, 30, or 40. In addition, the space need not be equally divided. Furthermore, it is also possible to perform division and selection over a plurality of times, like selecting one area from a plurality of divided areas, further dividing the selected area into a plurality of smaller areas, and selecting one of the plurality of smaller areas.

An example of dividing memory space A into 20 areas (classes) and determining one of the 20 areas (classes) by using the reference image displayed in FIG. 23B will be described below with reference to FIGS. 26 and 27. First of all, the reference image exemplarily shown in FIG. 23B is written in memory space B of the memory 106e. The information to be written includes the signal values of pixels, of the pixels (black and white pixels) constituting the reference image, whose coordinates in the x direction and the y direction are equal to those of the sensors 212 for AEC, and the coordinates in the x direction and the y direction. The pixels constituting the reference image include pixels at the same coordinates as those of all the AEC sensors 212. The signal values of the reference image are formed from 1-bit information per pixel. If the coordinates of the pixels constituting the reference image in the x direction and the y direction are periodical values, coordinate information itself may not be directly included in the data of the reference image. Even in this case, signal values and coordinate information can be written in pairs in the memory 106e. A determination value as a comparison result is stored in memory space C of the memory 106e. Referring to FIGS. 26A and 26B, the AEC data (memory space A) sorted according to the magnitudes of signal values, reference image data (memory space B), and the coordinates of comparison results in the x direction and the y direction and the determination values (memory space C) are all expressed by two bytes.

The storage order of coordinate information stored in memory space C is the same as that in memory space A. In memory space A, as the addresses in the memory increase for every six bytes, like (0x100000), (0x100006), (0x10000C), . . . , coordinates (250, 320), (230, 1240), (1570, 780), . . . are stored. In memory space C as well, as the addresses in the memory increase for every six bytes, like (0x300000), (0x300006), (0x30000C), . . . , coordinates (250, 320), (230, 1240), (1570, 780), . . . are stored.

When the reference image data is stored in memory space B, the comparison unit 106c searches memory space B for coordinate information matching the coordinates of data stored in memory space A. Upon obtaining the matching coordinate information, the comparison unit 106c checks a signal value associated with the coordinate information in memory space B, determines a determination value (comparison result) based on the signal value, and stores it as a determination value in correspondence with the same coordinate information in memory space C. In this case, if the signal value in memory space B is 1, the determination value is set to 1. If the signal value is 0, the determination value is set to 0. That the signal value corresponding to the coordinates of a comparison target in memory space B is 1 means that the signal value at the corresponding coordinates of AEC data stored in memory space A matches the signal value at the corresponding coordinates of the reference image stored in memory space B. In contrast to this, that the signal value corresponding to the coordinates of a comparison target in memory space B is 0 means that the signal value at the corresponding coordinates of AEC data stored in memory space A does not match the signal value at the corresponding coordinates of the reference image stored in memory space B. That is, to store 1 as a determination value means that a corresponding signal value of the ACE data stored in memory space A matches a corresponding signal value of the reference image. In addition, to store 0 as a determination value means that a corresponding signal value of the ACE data stored in memory space A does not match a corresponding signal value of the reference image.

For example, in the case shown in FIGS. 26A and 26B, coordinate information with a coordinate in the x direction being 250 and a coordinate in the y direction being 320 has been searched out in memory space B, and the signal value associated with the coordinate information is 0. In addition, 0 is stored as a determination value corresponding to coordinate information with the coordinate in memory C in the x direction being 250 and the coordinate in the y direction being 320. In addition, since the signal value corresponding to coordination information with a coordinate in the x direction being 3000 and a coordinate in the y direction being 2980 is 1 in memory space B, 1 is stored as a determination value corresponding to the coordinate information in memory space C.

The above comparison may be performed with respect to all the 20 areas (a) to (t) or may be performed with respect to some of them. More specifically, 20 areas (a) to (t) can include at least a non-object area image or a non-irradiation area image. Since the non-object area image and the non-irradiation area image cannot be used for AEC, it is efficient to exclude them from comparison targets. It is also efficient to exclude the above boundary area (an image in a class adjacent to a class to which a non-object area image belongs and an image in a class adjacent to a class to which a non-irradiation area image belongs) from comparison targets. Therefore, the signal processing unit 106a can be configured to compare the similarities between the reference image and some of a plurality of images generated by dividing the signals detected by a plurality of sensors 212 to a plurality of classes based on the signal values.

At the coordinates corresponding to a determination value of 1 on data stored in memory C, the signal value of the reference image stored in memory space B is 1. Therefore, coordinates corresponding to termination value of 1 on the data stored in memory space C indicate the coordinates of a region for AEC which is represented by the reference image.

Subsequently, the comparison unit 106c calculates the sum of determination values in memory space C in each area (class) subjected to comparison. This sum is an index for evaluating the similarity between an image in each area (class) and the reference image. The comparison unit 106c determines, as a region to be used for AEC, an area (class) exhibiting the largest sum of determination values, that is, an area (class) exhibiting the highest similarity with the reference image, and transmits information representing the area (class) to the monitoring unit 106b.

In steps S306 and S307, the monitoring unit 106b monitors the irradiation of radiation based on the signals detected by the monitoring sensors determined in step S305. More specifically, in step S306, the monitoring unit 106b computes an evaluation value (a value for evaluating the dose of irradiated radiation) such as the average value of signal values belonging to the area (class) stored in memory space A, which is specified in accordance with the information transmitted from the comparison unit 106c. In this case, the signal values belonging to the area (class) stored in memory space A, which is specified in accordance with the information transmitted from the comparison unit 106c are the signal values detected by the monitoring sensors. In step S307, the monitoring unit 106b determines whether the evaluation value computed in step S305 has exceeded a threshold. Upon determining that the evaluation has exceeded the threshold, the monitoring unit 106b issues an instruction to stop emission of radiation to the control circuit 102a in step S308. In response to this instruction, the control circuit 102a controls the radiation source 103 to stop the emission of radiation. On other hand, if the monitoring unit 106b determines that the evaluation value has not exceeded the threshold, the process returns to step S306.

The above embodiments have exemplified the case in which a non-object area and a non-irradiation area such as an implant portion exist. However, the present invention holds even if there are no non-object area and/or a non-irradiation area. For example, even if there is no non-object area, AEC monitoring should not be performed by using the sensor which has output the maximum signal value. If there is no non-object area, the sensor which has output the maximum signal value is regarded as a sensor indicating a specific region. In practice, however, a radiation source has an initial distribution, which may generate radiation with a very high output in a partial area. For various causes including such a case, the sensor which has output the maximum signal value may indicate an area different from the region targeted by the doctor or radiation technician. Likewise, if there is no non-irradiation area such as an implant portion, AEC monitoring should not be performed by using sensors in a specific range including the sensor which has output the minimum signal value. In this case, it is difficult to specify a region based on an output from the sensor which has output the minimum signal value because of the influence of noise components, and it is difficult to perform accurate AEC determination.

This embodiment is configured to determine a class for AEC (the sensors 212 used for AEC) by comparing an image in each class with a reference image (that is, pattern matching), and hence is highly resistance to noise. It is therefore possible to determine a region for AEC (that is, sensors to be used for AEC) with high accuracy.

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2014-152401 filed Jul. 25, 2014 and 2014-160799 filed Aug. 6, 2014, which are hereby incorporated by reference herein in their entirety.

What is claimed is:

1. A radiation imaging apparatus comprising:
a radiation detection unit including a plurality of sensors which detect radiation; and
a monitoring unit which monitors irradiation of radiation based on signals detected by the plurality of sensors,
wherein the monitoring unit determines a plurality of effective sensor candidates from the plurality of sensors, and determines effective sensor(s) from effective sensor candidates excluding certain effective sensor candidates of the plurality of effective sensor candidates, the certain effective sensor candidates being an effective sensor candidate which has detected a signal having a maximum value and an effective sensor candidate which has detected a signal having a minimum value, and
wherein the monitoring unit monitors irradiation of radiation based on signal(s) detected by the effective sensor(s).

2. The apparatus according to claim 1, wherein the monitoring unit determines the plurality of effective sensor candidates so as not to include a sensor which radiation enters without being transmitted through an object and a sensor which is not irradiated with radiation.

3. The apparatus according to claim 1, wherein the monitoring unit determines the effective sensor(s) from the plurality of effective sensor candidates in accordance with information set for obtaining a radiation image.

4. The apparatus according to claim 3, wherein the monitoring unit determines the effective sensor(s) from the plurality of effective sensor candidates in accordance with a monitoring condition, of a plurality of monitoring conditions registered in a database, which matches the information.

5. The apparatus according to claim 1, wherein the monitoring unit specifies the plurality of effective sensor candidates from selected sensors which have been selected from the plurality of sensors in accordance with information set for obtaining a radiation image, the plurality of effective sensor candidates being sensors excluding, from the selected sensors, a sensor which radiation enters without being transmitted through an object and a sensor which is not irradiated with radiation.

6. The apparatus according to claim 1, wherein the monitoring unit generates a histogram of values of signals from sensors selected from the plurality of sensors, and determines the plurality of effective sensor candidates based on the histogram.

7. The apparatus according to claim 6, wherein the monitoring unit determines, as an effective sensor, an effective sensor candidate which has detected a signal having a value within an arbitrary range from larger than 0% to smaller than 100%, with a signal having the maximum value being 100% and a signal having the minimum value being 0%.

8. The apparatus according to claim 1, wherein the monitoring unit stops emission of radiation based on a signal detected by the effective sensor.

9. The apparatus according to claim 1, wherein each of the plurality of sensors is also used as a pixel for obtaining a radiation image.

10. The apparatus according to claim 1, wherein the radiation detection unit further includes a readout unit configured to read out signals from the plurality of sensors, and the readout unit includes a driving unit configured to drive the plurality of sensors, amplification units configured to amplify signals provided from the plurality of sensors via signal lines, and a multiplexer configured to sequentially select signals provided from the amplification units.

11. The apparatus according to claim 10, wherein the readout unit further includes an AD converter configured to convert signals provided from the multiplexer into digital signals.

12. The apparatus according to claim 10, wherein the radiation detection unit includes a plurality of pixels for obtaining a radiation image, and some of the plurality of pixels are used as the plurality of sensors.

13. The apparatus according to claim 12, wherein the pixel includes a conversion element configured to output an electrical signal corresponding to an amount of incident radiation and a switch configured to connect the conversion element to a column signal line, and the amplifying unit amplifies a signal output to the column signal line.

14. A radiation imaging system comprising:
a radiation source configured to emit radiation; and
a radiation imaging apparatus, wherein the radiation imaging apparatus comprises:
a radiation detection unit including a plurality of sensors which detect radiation; and
a monitoring unit which monitors irradiation of radiation based on signals detected by the plurality of sensors,
wherein the monitoring unit determines a plurality of effective sensor candidates from the plurality of sensors, and determines effective sensor(s) from effective sensor candidates excluding certain effective sensor candidates of the plurality of effective sensor candidates, the certain effective sensor candidates being an effective sensor candidate which has detected a signal having a maximum value and an effective sensor candidate which has detected a signal having a minimum value, and
wherein the monitoring unit monitors irradiation of radiation based on signal(s) detected by the effective sensor(s).

15. A radiation imaging apparatus comprising:
a radiation detection unit including a plurality of sensors which detect radiation; and
a monitoring unit which monitors irradiation of radiation based on signals detected by the plurality of sensors,
wherein the monitoring unit determines a plurality of effective sensor candidates from the plurality of sensors, and determines effective sensor(s) from effective sensor candidates excluding certain effective sensor candidates of the plurality of effective sensor candidates, the certain effective sensor candidates being an effective sensor candidate which has detected a signal having a maximum value and an effective sensor candidate which has detected a signal having a minimum value, wherein the monitoring unit monitors irradiation of radiation based on signals detected by the effective sensors, and wherein the monitoring unit specifies the plurality of effective sensor candidates from selected sensors which have been selected from the plurality of sensors in accordance with information set for obtaining a radiation image, the plurality of effective sensor candidates being sensors excluding, from the selected sensors, a sensor which radiation enters without being transmitted through an object and a sensor which is not irradiated with radiation.

16. A radiation detection apparatus comprising:
a radiation detection unit including a plurality of sensors configured to detect radiation; and
a signal processing unit which processes signals detected by the plurality of sensors,
wherein the signal processing unit divides signals detected by the plurality of sensors into a plurality of classes based on signal values of the detected signals to generate a plurality of images respectively corresponding to the plurality of classes,
wherein the signal processing unit selects one image from the plurality of images based on similarity between each of at least some of the plurality of images with a reference image,
wherein the signal processing unit determines, as a monitoring sensor, a sensor which has detected signals forming the selected image, and
wherein the signal processing unit monitors irradiation of radiation based on a signal detected by the monitoring sensor.

17. The apparatus according to claim 16, wherein each of the plurality of images is a binary image formed by black pixels and white pixels, the black pixels being signals, of signals detected by the plurality of sensors, which have signal values other than 0, the white pixels being signals, of the signals detected by the plurality of sensors, which have a signal value of 0, and
wherein the reference image is a binary image constituted by black pixels and white pixels, and
wherein the signal processing unit evaluates the similarity based on the number of black pixels of each of the plurality of images which match black pixels of the reference image.

18. The apparatus according to claim 16, wherein the plurality of images include at least one of an image generated by signals detected by sensors which radiation enters without being transmitted through an object and an image generated by signals detected by sensors which are not irradiated with radiation, and
the at least one image is determined so as to exclude the image generated by the signals detected by the sensors which radiation enters without being transmitted through the object and the image generated by the signals detected by the sensors which are not irradiated with radiation.

19. The apparatus according to claim 18, wherein the at least one image is determined so as to exclude an image in a class adjacent to a class to which the image generated by the signals detected by the sensors which radiation enters without being transmitted through the object belongs and an image in a class adjacent to a class to which the image generated by the signals detected by the sensors which is not irradiated with radiation belongs.

20. The apparatus according to claim 16, wherein the signal processing unit selects the reference image from a plurality of reference images in accordance with information set for obtaining a radiation image.

21. The apparatus according to claim 16, wherein the signal processing unit stops emission of radiation based on a signal detected by the monitoring sensor.

22. The apparatus according to claim 16, wherein each of the plurality of sensors is used as a pixel for obtaining a radiation image.

23. A radiation imaging system comprising:
a radiation source configured to emit radiation; and
a radiation detection apparatus, wherein the radiation detection apparatus comprises:
a radiation detection unit including a plurality of sensors configured to detect radiation; and
a signal processing unit which processes signals detected by the plurality of sensors,
wherein the signal processing unit divides signals detected by the plurality of sensors into a plurality of classes based on signal values of the detected signals to generate a plurality of images respectively corresponding to the plurality of classes,
wherein the signal processing unit selects one image from the plurality of images based on similarity between each of at least some of the plurality of images with a reference image,
wherein the signal processing unit determines, as a monitoring sensor, a sensor which has detected signals forming the selected image, and
wherein the signal processing unit monitors irradiation of radiation based on a signal detected by the monitoring sensor.

24. A radiation imaging apparatus comprising:
a radiation detection unit including a plurality of sensors which detect radiation; and
a monitoring unit which monitors irradiation of radiation based on signals detected by the plurality of sensors,
wherein the monitoring unit determines effective sensor(s) from effective sensor candidates of a plurality of effective sensor candidates included in a plurality of sensors, the effective sensor candidates excluding certain effective sensor candidates of the plurality of effective sensor candidates, the certain effective sensor candidates being at least one of an effective sensor candidate which has detected a signal having a maximum value and an effective sensor candidate which has detected a signal having a minimum value, and
wherein the monitoring unit monitors irradiation of radiation based on signal(s) detected by the effective sensor(s).

25. The apparatus according to claim 24, wherein the monitoring unit determines the plurality of effective sensor candidates so as not to include a sensor which radiation enters without being transmitted through an object and a sensor which is not irradiated with radiation.

26. The apparatus according to claim 24, wherein the monitoring unit determines the effective sensor(s) from the plurality of effective sensor candidates in accordance with information set for obtaining a radiation image.

27. The apparatus according to claim 26, wherein the monitoring unit determines the effective sensor(s) from the plurality of effective sensor candidates in accordance with a monitoring condition, of a plurality of monitoring conditions registered in a database, which matches the information.

28. The apparatus according to claim 24, wherein the monitoring unit specifies the plurality of effective sensor candidates from selected sensors which have been selected from the plurality of sensors in accordance with information set for obtaining a radiation image, the plurality of effective sensor candidates being sensors excluding, from the selected sensors, a sensor which radiation enters without being transmitted through an object and a sensor which is not irradiated with radiation.

29. The apparatus according to claim 24, wherein the monitoring unit generates a histogram of values of signals from sensors selected from the plurality of sensors, and determines the plurality of effective sensor candidates based on the histogram.

30. The apparatus according to claim 24, wherein the monitoring unit determines, as an effective sensor, an effective sensor candidate which has detected a signal having a value within an arbitrary range from larger than 0% to smaller than 100%, with a signal having the maximum value being 100% and a signal having the minimum value being 0%.

31. The apparatus according to claim 24, wherein the monitoring unit stops emission of radiation based on a signal detected by the effective sensor.

32. The apparatus according to claim 24, wherein each of the plurality of sensors is also used as a pixel for obtaining a radiation image.

33. The apparatus according to claim 24, wherein the radiation detection unit further includes a readout unit configured to read out signals from the plurality of sensors, and the readout unit includes a driving unit configured to drive the plurality of sensors, amplification units configured to amplify signals provided from the plurality of sensors via signal lines, and a multiplexer configured to sequentially select signals provided from the amplification units.

34. The apparatus according to claim 33, wherein the readout unit further includes an AD converter configured to convert signals provided from the multiplexer into digital signals.

35. The apparatus according to claim 33, wherein the radiation detection unit includes a plurality of pixels for obtaining a radiation image, and some of the plurality of pixels are used as the plurality of sensors.

36. The apparatus according to claim 35, wherein the pixel includes a conversion element configured to output an electrical signal corresponding to an amount of incident radiation and a switch configured to connect the conversion element to a column signal line, and the amplifying unit amplifies a signal output to the column signal line.

37. A radiation imaging system comprising:
a radiation source configured to emit radiation; and
a radiation imaging apparatus as defined in claim 24.

38. A radiation imaging apparatus comprising:
a radiation detection unit including a plurality of sensors which detect radiation; and
a monitoring unit which monitors irradiation of radiation based on signals detected by the plurality of sensors,
wherein the monitoring unit determines effective sensor(s) from effective sensor candidates of a plurality of effective sensor candidates included in a plurality of sensors, the effective sensor candidates excluding certain effective sensor candidates of the plurality of effective sensor candidates, the certain effective sensor candidates being at least one of an effective sensor candidate which has detected a signal having a maximum value and an effective sensor candidate which has detected a signal having a minimum value,
wherein the monitoring unit monitors irradiation of radiation based on signals detected by the effective sensors, and
wherein the monitoring unit specifies the plurality of effective sensor candidates from selected sensors which have been selected from the plurality of sensors in accordance with information set for obtaining a radiation image, the plurality of effective sensor candidates being sensors excluding, from the selected sensors, a sensor which radiation enters without being transmitted through an object and a sensor which is not irradiated with radiation.

39. A radiation detection apparatus comprising:
a radiation detection unit including a plurality of sensors configured to detect radiation; and
a signal processing unit which processes signals detected by the plurality of sensors,
wherein the signal processing unit generates an image corresponding to signals detected by the plurality of sensors,
wherein the signal processing unit determines a monitoring sensor from the plurality of sensors based on similarity between the image and a reference image, and
wherein the signal processing unit monitors irradiation of radiation based on a signal detected by the monitoring sensor.

40. The apparatus according to claim 39, wherein the signal processing unit divides the signals detected by the plurality of sensors into a plurality of classes based on signal values of the detected signals to generate a plurality of images respectively corresponding to the plurality of classes,
wherein the signal processing unit selects one image from the plurality of images based on similarity between each of at least some of the plurality of images with the reference image,
wherein the signal processing unit determines, as the monitoring sensor, a sensor which has detected signals forming the selected image.

41. The apparatus according to claim 40, wherein the plurality of images include at least one of an image generated by signals detected by sensors which radiation enters without being transmitted through an object and an image generated by signals detected by sensors which are not irradiated with radiation, and
wherein the at least one image is determined so as to exclude the image generated by the signals detected by the sensors which radiation enters without being transmitted through the object and the image generated by the signals detected by the sensors which are not irradiated with radiation.

42. The apparatus according to claim 40, wherein the at least one image is determined so as to exclude an image in a class adjacent to a class to which the image generated by the signals detected by the sensors which radiation enters without being transmitted through the object belongs and an image in a class adjacent to a class to which the image generated by the signals detected by the sensors which is not irradiated with radiation belongs.

43. The apparatus according to claim 39, wherein each of the plurality of images is a binary image formed by black pixels and white pixels, the black pixels being signals, of signals detected by the plurality of sensors, which have signal values other than 0, the white pixels being signals, of the signals detected by the plurality of sensors, which have a signal value of 0, and
wherein the reference image is a binary image constituted by black pixels and white pixels, and
wherein the signal processing unit evaluates the similarity based on the number of black pixels of each of the plurality of images which match black pixels of the reference image.

44. The apparatus according to claim 39, wherein the signal processing unit selects the reference image from a plurality of reference images in accordance with information set for obtaining a radiation image.

45. The apparatus according to claim 39, wherein the signal processing unit stops emission of radiation based on a signal detected by the monitoring sensor.

46. The apparatus according to claim 39, wherein each of the plurality of sensors is used as a pixel for obtaining a radiation image.

47. A radiation imaging system comprising:
a radiation source configured to emit radiation; and
a radiation detection apparatus as defined in claim 39.

* * * * *